United States Patent
Voros et al.

(10) Patent No.: US 8,970,578 B2
(45) Date of Patent: Mar. 3, 2015

(54) SYSTEM AND METHOD FOR LESION-SPECIFIC CORONARY ARTERY CALCIUM QUANTIFICATION

(76) Inventors: Szilard Voros, Atlanta, GA (US); Zhen Qian, Altanta, GA (US)

(*) Notice: Subject to any disclaimer, the term of this patent is extended or adjusted under 35 U.S.C. 154(b) by 574 days.

(21) Appl. No.: 12/643,962

(22) Filed: Dec. 21, 2009

(65) Prior Publication Data

US 2010/0156898 A1   Jun. 24, 2010

Related U.S. Application Data

(60) Provisional application No. 61/139,165, filed on Dec. 19, 2008.

(51) Int. Cl.
| | |
|---|---|
| G06T 15/00 | (2011.01) |
| A61B 6/00 | (2006.01) |
| A61B 5/02 | (2006.01) |
| G06T 7/00 | (2006.01) |
| G06T 15/08 | (2011.01) |
| A61B 6/03 | (2006.01) |
| G06F 19/00 | (2011.01) |

(52) U.S. Cl.
CPC ............ *A61B 6/504* (2013.01); *A61B 5/02007* (2013.01); *G06T 7/0012* (2013.01); *G06T 15/08* (2013.01); *A61B 6/032* (2013.01); *A61B 6/5288* (2013.01); *G06F 19/321* (2013.01); *G06F 19/3431* (2013.01); *G06T 2200/24* (2013.01); *G06T 2207/10081* (2013.01); *G06T 2207/30048* (2013.01)
USPC ........................... 345/419; 382/128; 382/131

(58) Field of Classification Search
USPC .................................. 345/419; 382/128, 131
See application file for complete search history.

(56) References Cited

U.S. PATENT DOCUMENTS

| | | | | |
|---|---|---|---|---|
| 5,319,551 | A * | 6/1994 | Sekiguchi et al. ............ | 382/131 |
| 6,591,004 | B1 * | 7/2003 | VanEssen et al. ............ | 382/154 |
| 7,940,977 | B2 * | 5/2011 | Begelman et al. ............ | 382/133 |
| 2007/0103464 | A1 * | 5/2007 | Kaufman et al. ............ | 345/424 |
| 2007/0142726 | A1 * | 6/2007 | Carney et al. ................ | 600/481 |
| 2007/0165949 | A1 * | 7/2007 | Sinop et al. .................. | 382/173 |

(Continued)

FOREIGN PATENT DOCUMENTS

WO    2007058997 A2    5/2007

OTHER PUBLICATIONS

International Search Report and Written Opinion of PCT/US2009/069081, dated Apr. 19, 2010.

*Primary Examiner* — Xiao M. Wu
*Assistant Examiner* — Todd Buttram
(74) *Attorney, Agent, or Firm* — Nelson Mullins Riley & Scarborough LLP

(57) ABSTRACT

Methods and systems utilizing the data provided by a non-contrast-enhanced CAC scan that is left unused by the "whole-heart" Agatston or volume scores. Agatston and volume scores summarize overall coronary calcium burden, but do not show the number of vessels involved, the geographic distribution of the lesions, the size and shape of the individual lesions and the distance of the lesions from the coronary ostium. The methods and systems described herein extract and use the enhanced information provided by 3-D CAC scan data and significantly increases its clinical predictive value by providing vessel and lesion specific CAC scores which are superior to the whole-heart Agatston and volume scores in predicting obstructive Coronary artery disease (CAD).

27 Claims, 12 Drawing Sheets

(56) References Cited

U.S. PATENT DOCUMENTS

| | | |
|---|---|---|
| 2008/0101674 A1* | 5/2008 | Begelman et al. ............ 382/130 |
| 2008/0159610 A1 | 7/2008 | Haas et al. |
| 2009/0086314 A1* | 4/2009 | Namba et al. ................. 359/383 |
| 2009/0136106 A1* | 5/2009 | Roberts et al. ................ 382/130 |
| 2010/0010797 A1* | 1/2010 | Bittner et al. ................... 703/11 |
| 2010/0189320 A1* | 7/2010 | Dewaele ....................... 382/128 |
| 2010/0220917 A1* | 9/2010 | Steinberg et al. ............. 382/134 |
| 2010/0278405 A1* | 11/2010 | Kakadiaris et al. ........... 382/131 |
| 2010/0278735 A1* | 11/2010 | Waxman et al. ............... 424/9.1 |

* cited by examiner

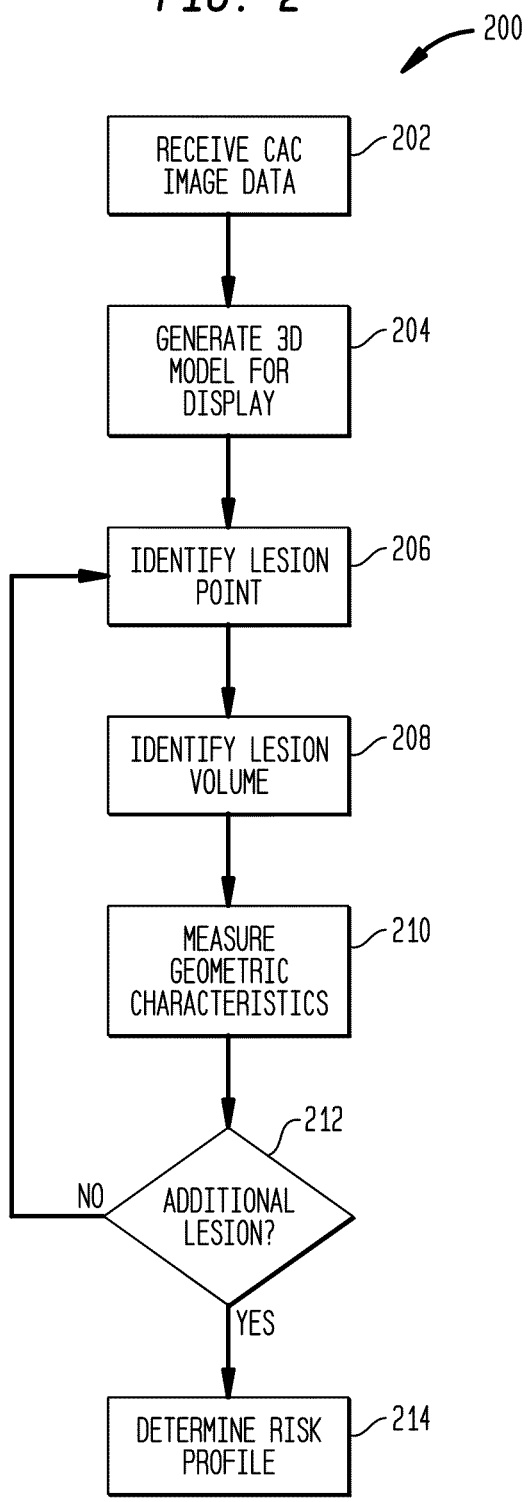

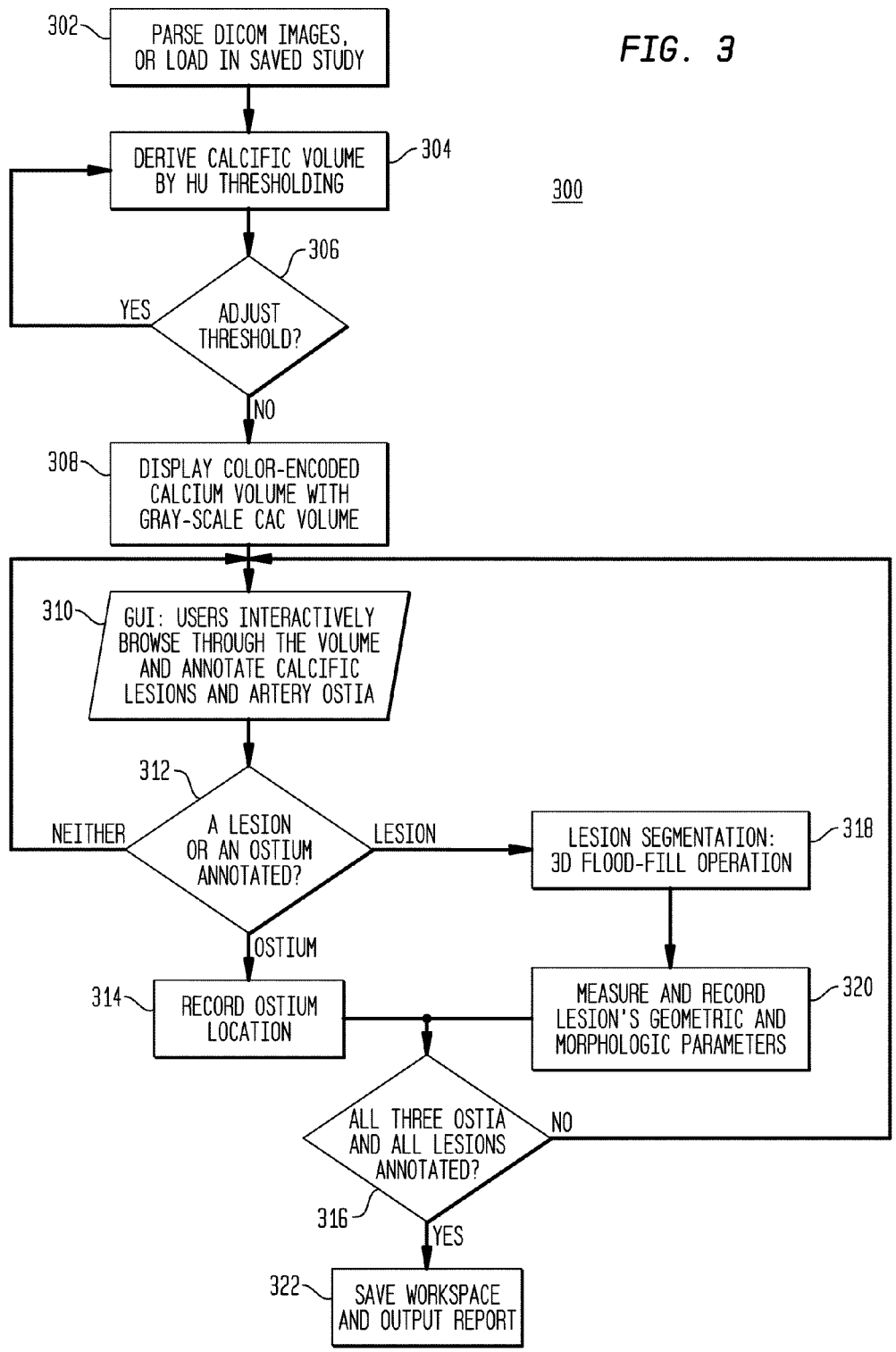

FIG. 8

Calcium Scoring Report - All units are in mm
Study name: XXXXXX,                Date: 2009/12/1                    Time: 9: 1:25
Total plaque number in LM is: 1
  Lesion 1: Volume    Agatston Score    Agatston Score3D   Length   Width   Distance To   LM Ostium   HU_Max   HU_Mean
            56.09           71.49              74.75       12.25    2.92                    10.82      499     291.36
 - LM Total: Volume   Agatston Score    Agatston Score3D
             56.09          71.49              74.75
 - LM Max:   Volume   Agatston Score    Agatston Score3D   Length   Width   Distance To   LM Ostium   HU_Max   HU_Mean
             56.09          71.49              74.75       13.25    2.02                    10.82      499
Total plaque number in LAD is: 4
  Lesion 1: Volume    Agatston Score    Agatston Score3D   Length   Width   Distance To   LAD Ostium  HU_Max   HU_Mean
            61.72           77.32              87.29       11.81    3.34                    10.70      559     292.97
  Lesion 2: Volume    Agatston Score    Agatston Score3D   Length   Width   Distance To   LAD Ostium  HU_Max   HU_Mean
            28.55           27.35              28.55        5.71    2.45                    19.01      386     269.97
  Lesion 3: Volume    Agatston Score    Agatston Score3D   Length   Width   Distance To   LAD Ostium  HU_Max   HU_Mean
             3.60            2.40               2.40        1.87    0.78                    23.17      280     246.07
  Lesion 4: Volume    Agatston Score    Agatston Score3D   Length   Width   Distance To   LAD Ostium  HU_Max   HU_Mean
            18.26           27.46              24.35        4.49    1.71                    26.33      458     300.80
 - LAD Total:Volume   Agatston Score    Agatston Score3D
            112.13          129.53             137.59
 - LAD Max:  Volume   Agatston Score    Agatston Score3D   Length   Width   Distance To   LAD Ostium  HU_Max   HU_Mean
            61.72           77.32              82.29       11.83    3.54                    10.70      359
Total plaque number in LCX is: 1
  Lesion 1: Volume    Agatston Score    Agatston Score3D   Length   Width   Distance To   LCX Ostium  HU_Max   HU_Mean
            21.60           23.40              28.80        0.54    1.89                    19.01      590     275.49
 - LCX Total:Volume   Agatston Score    Agatston Score3D
            21.80           23.40              28.90
 - LCX Max:  Volume   Agatston Score    Agatston Score3D   Length   Width   Distance To   LAD Ostium  HU_Max   HU_Mean
            21.60           23.40              28.80        6.59    1.63                    25.01      500
Total plaque number in RCA is: 5
  Lesion 1: Volume    Agatston Score    Agatston Score3D   Length   Width   Distance To   RCA Ostium  HU_Max   HU_Mean
             4.63            3.96               4.53        1.84    0.92                     6.35      200     240.22
  Lesion 2: Volume    Agatston Score    Agatston Score3D   Length   Width   Distance To   RCA Ostium  HU_Max   HU_Mean
             6.77            4.37               6.52        6.71    0.88                    23.80      336     182.89
  Lesion 3: Volume    Agatston Score    Agatston Score3D   Length   Width   Distance To   RCA Ostium  HU_Max   HU_Mean
             7.46            3.80               4.97        3.38    1.28                    29.80      233     163.24
  Lesion 4: Volume    Agatston Score    Agatston Score3D   Length   Width   Distance To   RCA Ostium  HU_Max   HU_Mean
             8.09            2.06               2.06        1.94    0.58                    34.13      282     228.78
  Lesion 5: Volume    Agatston Score    Agatston Score3D   Length   Width   Distance To   RCA Ostium  HU_Max   HU_Mean
             4.89            4.71               4.89        1.72    0.92                    35.58      342     282.37
 - RCA Total:Volume   Agatston Score    Agatston Score3D
            29.93           18.00              23.06
 - RCA Max:  Volume   Agatston Score    Agatston Score3D   Length   Width   Distance To   LAD Ostium  HU_Max   HU_Mean
             9.77            4.87               6.52        6.71    1.29                     6.25      342
Total calcified volume is: 239.62
Total Agatston score is: 242.43
Total Agatston score in 3D is: 264.20

FIG. 10

| | | | 50% STENOSIS | | | | | | 70% STENOSIS | | | |
|---|---|---|---|---|---|---|---|---|---|---|---|---|
| | AUC | CUT-POINT | SENS | SPEC | PPV | NPV | AUC | CUT-POINT | SENS | SPEC | PPV | NPV |
| WH-AgSc | 0.58 | 986 | 31.6% | 92.6% | 90% | 39.1% | 0.66 | 790 | 48.5% | 82.4% | 64% | 71.2% |
| WH-AglSc | | 100 | 70.5% | 36.7% | 69.4% | 37.9% | | 100 | 77.1% | 37.5% | 43.5% | 72.4% |
| WH-AgSc | | 400 | 47.5% | 60% | 70.7% | 36% | | 400 | 60% | 64.3% | 51.2% | 72% |
| WH-VolSc | 0.59 | 894 | 29.8% | 92.6% | 89.5% | 38.5% | 0.66 | 484 | 57.6% | 76.5% | 61.3% | 73.6% |
| VS-AgSc | 0.72 | 149 | 66.3% | 74.8% | 57.9% | 81% | 0.77 | 104 | 86.1% | 58.3% | 26.5% | 96% |
| VS-VolSc | 0.72 | 125 | 69.9% | 73.6% | 58% | 82.4% | 0.77 | 173 | 72.2% | 75.2% | 33.8% | 93.9% |
| MAX LS-AgSc | 0.71 | 76 | 73.5% | 64.8% | 52.1% | 82.4% | 0.75 | 182 | 61.1% | 82.5% | 37.9% | 92.4% |
| MAX LS-VolSc | 0.72 | 132 | 50.6% | 88.1% | 68.9% | 77.3% | 0.76 | 154 | 61.1% | 83.5% | 39.3% | 92.5% |
| MEAN LS-AgSc | 0.68 | 42 | 61.4% | 74.8% | 56% | 78.8% | 0.7 | 77 | 55.6% | 80.6% | 33.3% | 91.2% |
| MEAN LS-VolSc | 0.68 | 50 | 62.7% | 74.2% | 55.9% | 79.2% | 0.7 | 41 | 72.2% | 65.5% | 26.8% | 93.1% |

SYSTEM AND METHOD FOR LESION-SPECIFIC CORONARY ARTERY CALCIUM QUANTIFICATION

CROSS-REFERENCE TO RELATED APPLICATIONS

This application claims the benefit of U.S. provisional Application Ser. No. 61/139,165, entitled, "System and Method for Lesion-Specific Coronary Artery Calcium Quantification", filed on Dec. 19, 2008.

TECHNICAL FIELD

The present system and method is a lesion-specific quantification tool for coronary artery calcium scans that can enhance or supplant other predictive indicators.

BACKGROUND OF THE INVENTION

Atherosclerosis is the leading cause of morbidity and mortality worldwide. It is a complex disease initiated and propagated by lipoprotein deposition and inflammation. Later stages of atherosclerosis are characterized by progressive deposition of calcium in the coronary arterial vessel-wall. Histopathology, computed tomography and intravascular ultrasound studies have confirmed that the extent of coronary calcification is closely correlated to the atherosclerosis plaque burden.

A cardiac tomography (CT) based coronary artery calcium (CAC) scan is a non-contrast-enhanced, three dimensional imaging technique that has been introduced as a non-invasive, low-radiation method for the assessment of the overall coronary arterial atherosclerotic burden, by quantifying calcium in the coronary vasculature. CAC has been validated to be independent of, and additive to, the Framingham Risk Score (FRS) in predicting major cardiovascular events. CAC is also considered safer and more appropriate for the primary prevention setting than invasive modalities, such as intravascular ultrasound (IVUS), and non-invasive and high-radiation modalities, such as CT angiography.

A three dimensional CAC image volume contains a large amount of clinically relevant information, such as the geometric and morphologic characteristics of each calcific lesion, which can be of high diagnostic and therapeutic value. However, current measurements of CAC, such as the Agatston score and the volume score, only quantify the whole-heart calcium burden.

SUMMARY OF THE INVENTION

Embodiments of the system and method described herein utilize the significantly greater data provided by a non-contrast-enhanced CAC scan; data that is left unused by the "whole-heart" Agatston or volume scores. While the Agatston score and volume score summarize overall coronary calcium burden, they are blind to the number of vessels involved, to the geographic distribution of the lesions, to the size and shape of the individual lesions and to the distance of the lesions from the coronary ostium. However, such information is inherently present in these clinically acquired scans. Embodiments of the systems and methods described herein extract and use the enhanced information provided by 3-D CAC scan data to improve prediction and assessment of cardiac risk.

Systems and methods described herein demonstrate that utilizing lesion-specific CAC (LS-CAC) and distance-weighted lesion-specific CAC (DWLS-CAC) improves prediction and assessment of obstructive coronary artery disease and prediction of cardiovascular events. Accordingly, these systems and methods significantly increase the clinical predictive value of traditional coronary artery calcium scanning.

An advantage of the systems and methods described herein is the ability to use standard imaging protocol. Embodiments of the lesion-specific calcium scoring systems and methods work on datasets acquired with typical clinical imaging protocols on conventional CT scanners. There is no need to modify the CT hardware or update the imaging protocol. Accordingly, there is no increased radiation exposure for the patients.

The described systems and methods also achieve fast semi-automatic calcific lesion-labeling and fully automated geometric and morphologic lesion measurements. Embodiments use a graphical user interface with automatic 3D propagation algorithm, to enable users to analyze a CAC volume rapidly (e.g., within 5 minutes), which is similar to, or even faster than using conventional CAC software while providing enhanced diagnostic capability.

In one embodiment, the system and method presents traditional measures such as total Agatston and volume scores as well as enhanced information comprising: statistics specific to each individual, such as each lesion's individual Agatston score, volume score, length, width, average and maximum attenuation values in Hounsfield unit (HU), as well as the distance of each lesion from corresponding vessel's ostium. These lesion-specific measurements highly correlate with the instances of coronary artery stenosis, and plaque volumes and compositions. Using a Naïve Bayesian approach, a distance-weighted measurement of the lesion-specific CAC was developed. This lesion specific CAC is more predictive of cardiovascular events compared to the overall CAC scores.

BRIEF DESCRIPTION OF DRAWINGS

The claimed subject matter is described with reference to the accompanying drawings. A brief description of each figure is provided below. Elements with the same reference number in each figure indicated identical or functionally similar elements. Additionally, the left-most digit(s) of a reference number indicate the drawing in which the reference number first appears.

FIG. 2 is a flowchart of an embodiment of a method for lesion-specific CAC quantification.

FIG. 3 is a flowchart of another embodiment of a method for lesion-specific CAC quantification.

FIG. 8 is an exemplary report highlighting details quantified by the systems and methods described herein.

FIG. 10 depicts a ROC curve analysis associated with the ROC curve depicted in FIG. 9.

DETAILED DESCRIPTION

Figure 1:
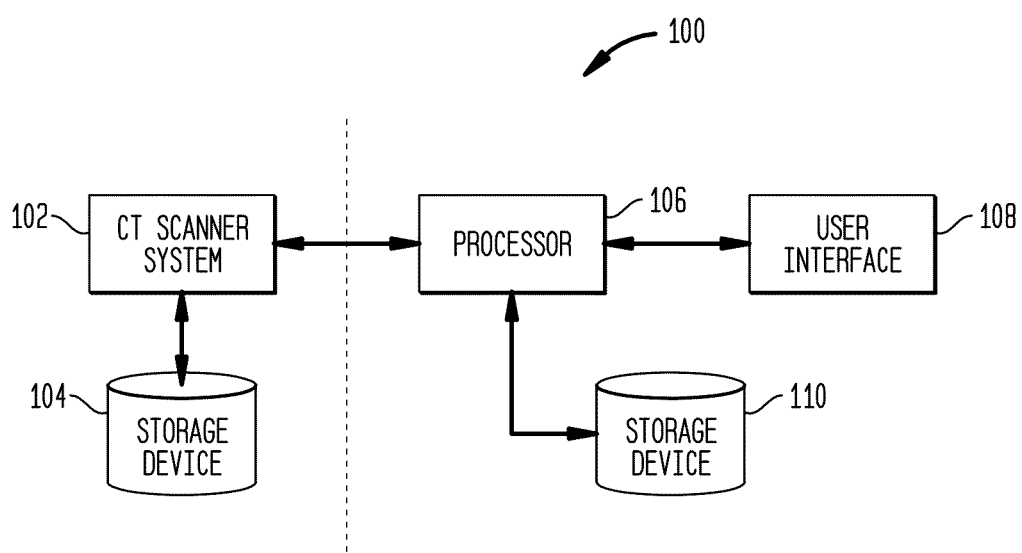
FIG. 1 is a block diagram of an embodiment of the system for lesion-specific CAC quantification.

Conventional CAC image volume analysis reduces the three-dimensional (3D) volume, to a stack of two-dimensional (2D) slices that form the 3D volume to facilitate processing. The stack 2D slices of 3D data are evaluated and used to identify and quantify the presence of artery calcium, indicative of atherosclerosis. Typically, the presence of calcium within the CAC image volume is evaluated as a whole to determine the calcium burden on the heart depicted in the CAC image volume. These conventional techniques ignore the position of the calcium lesions as well as the geometry and size of individual calcium lesions. To minimize processing, risks of atherosclerosis are evaluated based upon these 2D images and averaged data.

In contrast, systems and methods described herein use the 3D volume of image data without reducing it to 2D data, avoiding potential errors introduced by representation of 3D data using sets of 2D images. For example, when 3D data is treated as a stack of 2D images, artifacts, such as lesions of calcium, whose major axis are aligned with the axis of the stack of 2D images may appear as a relatively small artifact in each 2D image, but may extend through a significant number of images. For a lengthy, but narrow lesion aligned with the axis of the stack of 2D images, only a small cross-section of the lesion would appear in each 2D image. A lesion may be overlooked or identified as relatively minor, even though it has significant length, due to the orientation of the artifact and the stack of 2D images. If the cross-section is sufficiently narrow, the appearance of the lesion in each 2D image could be filtered as noise within the data, resulting in the elimination of a significant lesion from the data and a significant, false reduction in the calculated risk. Maintaining the 3D nature of the image volume eliminates this potential source of error in image analysis.

In further embodiments, the systems and methods described herein analyze CAC image volumes on a lesion specific basis, evaluating individual lesions present within the CAC volume, rather than analyzing the presence of calcium within the CAC volume representing the heart as a whole. In conventional methodologies, lesions appearing throughout the heart are evaluated and averaged to determine the calcification of the volume and risk to the heart. While averaging may generally provide reasonable predictions of the effects of the lesions, in situations where the lesions vary significantly, averaging may not accurately reflect the risks to the heart. For example, if the set of lesions includes a single large lesion and one or more smaller lesions, the average of the set will appear the same as a set of mid-sized lesions; however, the risk of that large lesion negatively impacting the heart is significantly greater. In contrast, in embodiments of the lesion-specific CAC quantification systems and methods, lesions are evaluated individually, such that the risk posed by the large lesion is recognized and reflected in the resulting analysis and risk profile. As used herein, the term risk profile means data indicative of the risk of a negative result, e.g. a coronary event or other negative impact of the presence of a lesion.

In other embodiments, the size, geometry and position of individual lesions is analyzed to provide a more accurate risk profile associated with the lesions. For example, lesions located proximate to an artery origin are more likely to adverse effects than those which are located distal from the artery origin. In addition, those lesions that protrude further into the ostium of an artery, causing a greater obstruction of the ostium, are more likely to result in adverse effects on the imaged individual than lesions that protrude only minimally into the ostium itself. By analyzing not just statistics describing the average presence of calcium in the CAC volume, but rather lesion specific information describing geometry, size and/or location of each individual lesion, the systems and methods described herein increase accuracy of predictions of risk to the individual imaged by the CAC volume.

FIG. 1 is a block diagram of an embodiment of a system 100 for lesion-specific CAC quantification, also referred to here in as LS-CAC quantification. In an exemplary embodiment, the system 100 includes a CT scanner system 102. As used herein, the term "exemplary" indicates a sample or example. It is not indicative of preference over other aspects or embodiments. The CT scanner is used in a conventional manner to scan or image a portion of the human body, in particular the coronary system, resulting in CAC image data. In an embodiment, the CAC image data is maintained in a first storage device 104 associated with the CT scanner system 102. The CAC image data can be maintained for later processing and analysis. As used herein the term storage device includes any suitable form of memory, including but not limited to static memory such as erasable programmable read only memory (EPROM), electronically erasable programmable read only memory (EEPROM), flash or bubble memory, hard disk drive, CD-ROM, a USB drive, tape drive or any combination of static memory and dynamic memory.

In another embodiment, the CAC image data is transmitted from the first storage device 104 to a processor 106 that performs lesion specific analysis of the CAC image data. In an alternate embodiment, the image data is provided directly from the CT scanner system 102 to the processor 106. Although system 100 is depicted as including a CT scanner system 102 in connection with the processor 106 that performs lesion-specific CAC quantification, the CT scanner system 102 may be completely independent, such that CAC image data is provided for processing, but no direct connection occurs between the CT scanner system 102 and the processor 106. The processor 106 can be implemented using a microprocessor, microcontroller, or central processor unit (CPU) chip and printed circuit board (PCB). Alternatively, the processor 106 can include an application specific integrated circuit (ASIC), programmable logic controller (PLC), programmable logic device (PLD), digital signal processor (DSP), or the like In an embodiment, the processor 106 is encoded with a method for lesion-specific analysis of the CAC image data as a 3D volume. As discussed above, such image data is typically analyzed as 2D slices of the 3D volume represented by the image data. Conventional systems analyze CT image data as a stack of 2D images to facilitate processing. In contrast, embodiments of the system 100 for lesion-specific CAC quantification, analyze the image data as a 3D volume of data. This 3D analysis avoids the inaccuracies introduced in analysis due to the limitations of 2D analysis.

In embodiment, the system 100 includes a user interface 108. In an embodiment, the user interface 108 includes a monitor, LED screen, touch screen or other display mechanism that displays 3D CAC image data. The user interface 108 can also include input devices such as a keyboard, mouse, trackball, pointer or any other input device. The user interface 108 allows users (e.g., physicians or technicians) to view the 3D CAC image data. As described in further detail below, through the user interface 108 users can move through the 3D CAC image data, and identify lesions. In a further embodiment, users utilize a cursor to identify a lesion by selecting point on the displayed image. Based upon the value of the selected point, the processor 106 processes the 3D CAC image data to determine the boundaries of the identified lesion. In an alternative embodiment, the processor 106 is able to identify lesions within the 3D CAC image data without requiring selection of initial points by users.

In a further embodiment, the user interface 108 depicts the selected lesion boundaries, such that the user can view the lesion geometry. In other embodiments, the user interface 108 provides users with the ability to adjust or confirm the presented boundaries of the lesion. In still other embodiments, the user interface 108 provides users with the opportunity to identify the relative location of the identified lesion. For example, the user can indicate that the lesion corresponds to the left main ostium using the user interface 108.

In other embodiments, the identification of lesions and associated information regarding the lesion location is stored along with the 3D CAC image data in a second storage device 110. Although the system 100 is depicted with two separate storage devices, 104, 110, a number of storage devices can be utilized with the system 100. The resulting information regarding location and geometry of lesions within the 3D CAC image can be further evaluated by the processor 106 to determine a risk profile for the individual and heart scanned to produce the 3D CAC image data. The resulting risk profile can be maintained in the storage device 110 and/or displayed to a user via the user interface 108.

Referring now to FIG. 2, an exemplary methodology for lesion-specific CAC quantification is illustrated. At step 202, CAC image data is obtained, either from a CT scanner system 102 or storage device 104. For example, a user can utilize the user interface 108 to select a particular CAC image data set from a storage device 104 for analysis and processing. At step 204, the processor 106 generates a model for display from the CAC image data. In particular, the CAC image date is transformed, such that the calcium levels are illustrated in the model.

In an embodiment, a user identifies a lesion within the displayed model via the user interface at step 206. For example, the user can select a point, or pixel, on the display, clicking or otherwise selecting the point to indicate the presence of a lesion at that point. The selected pixel corresponds to a voxel within the 3D CAC image data, where a voxel is a three-dimensional pixel. A voxel represents a quantity of 3D data just as a pixel represents a point or cluster of points in 2D data. In another embodiment, the processor 106 identifies likely lesions based upon the 3D CAC image data. In a further embodiment, a user confirms or rejects processor 106 identified lesions.

At step 208, the processor 106 maps the boundaries of the identified lesion within the displayed model. In an embodiment, the boundaries are determined through the use of a flood-fill operation. For example, each voxel adjacent to the user-selected voxel is evaluated. If the value of the adjacent voxel is determined to be within a predetermined range, the voxel is identified as part of the lesion identified by the user-selected voxel. This adjacent voxel is marked as a lesion, and voxels adjacent to this newly identified lesion voxel or analyzed to determine whether they too are a part of the lesion. If the adjacent voxel is not part of the lesion, the processor 106 continues to evaluate the remaining voxels adjacent to the earlier identified lesion voxel, until all of the edges of the lesion have been identified.

At this point, a 3D map or model of the user identified lesion volume has been created. At step 210, the geometric characteristics of the identified lesion are measured. For example, the processor 106 can calculate the width, length, height and location of the lesion with respect to one or more arteries. At step 212, a determination is made as to whether there are addition lesions to process. In an embodiment, the user indicates via the user interface 108 that identification of lesions is complete or continues to select additional points identifying lesions. If further lesions are to be identified, the process returns to step 206; if all the lesions are selected or identified, the process continues to step 214.

In an embodiment, at step 214, the processor 216 determines a risk profile associated with the identified and mapped lesions. In a further embodiment, in addition to the analysis of the lesions as a whole, the processor 106 evaluates the individual lesions, including lesion geometry and location to generate a risk profile and analysis of the CAC volume.

FIG. 3 illustrates another embodiment of a methodology 300 for lesion-specific CAC quantification. At step 302, the CAC volume from image files in (Digital Imaging and Communications in Medicine (DICOM) format are parsed and loaded. In an alternative embodiment of the methodology, there is an option to load in image data and LS-CAC quantification results from previously saved studies. For example, LS-CAC results can be maintained in the storage device for further analysis.

At step 304, the CAC image is converted to a binary calcium volume based on HU thresholding. This conversion is based upon selection of an intensity threshold of the calcific lesions. In an embodiment, a conventional threshold equaling 130 HU is defined as the default value. In other embodiments the default intensity threshold is selectable by the user via the user interface 108. In one embodiment, at step 306, a determination is made as to whether an adjustment to the intensity threshold is necessary to allow for identification of lesions within the calcium volume. If yes, the intensity threshold is adjusted and the process returns to step 304 where the calcific volume derived again. Once an appropriate intensity threshold is selected, the calcific volume is displayed at step 308.

In an embodiment, in the converted volume, calcific lesions are displayed by overlaying the color-encoded binary calcium volume onto the gray-scale CAC volume. In this example, the CAC volume is depicted in gray-scale, where the intensity of a particular pixel indicates the density of calcium for the voxel within the CAC volume. Accordingly, areas of greater calcium density, such as lesions will appear as higher intensity areas in the display of the user interface 108. In an embodiment, the intensity threshold selected above is a value such that calcium densities that are too low to be part of a lesion are not shown on the display. By selecting the proper threshold, the boundaries of lesions are easier more noticeable on the display and easier to detect. Once a lesion is positively identified it may be encoded in color to further hi-light the lesion.

In an embodiment, a graphical user interface 108 (GUI) allows users to easily browse through the entire 3D CAC volume at step 310. By interactively clicking on the GUI's three orthogonal cross-section views, described in detail below, users are able to localize and annotate the four major coronary arteries' ostia, i.e., left main (LM) ostium, left anterior descending (LAD) and left circumflex (LCx) ostium, and right coronary artery (RCA) ostium. At step 312, a determination is made whether the user identified and annotated an ostium, or lesion. If the user identified and annotated an ostium, the position of the ostium is recorded with respect to the CAC volume at step 314.

At step 316, a determination is made as to whether all of the ostium and lesions have been identified and annotated. If not, the process returns to step 310, where users can continue to identify ostium or can interactively localize calcific lesions and annotate their corresponding arteries, i.e., LM, LAD, LCx, and RCA by clicking and specifying a seed point within each coronary calcific lesion via the user interface 108. For lesions that cover two or more arteries, the corresponding artery is defined as the artery that is more proximal to the lesion. For example, if a lesion locates at the ostium of LAD and LCx, and covers all three LM, LAD and LCx arteries, this lesion is labeled as LM.

If the user selects another point, identified as a lesion at step 312, then after selection of a user-specified seed point as a lesion, a 3D 6-connected flood-fill operation is applied to segment the 3D calcific lesion at step 318. This 3D flood-fill operation automatically propagates through slices in 3D using a 6-connectiveness criterion, which will be explained in detail below. As a result of this flood-fill, users are not required to label the lesion slice by slice, as required in conventional 2D analysis of CAC volume. In this manner, the described methodology 300 can vastly expedite the image analysis process.

Another advantage of the described 3D approach is that the de-noising method using volume-size-thresholding in 3D is more accurate than in 2D. In conventional 2D approaches, for de-noising purposes, lesions in a single 2D slice with volume size smaller than 1 mm$^2$ are treated as noise and discarded. However, this is may be inaccurate, since these small-sized 2D lesions could be parts of larger 3D lesions. As discussed above, a long but narrow lesion might appear as less than 1 mm$^2$ in multiple slices. The lesion would be classified as noise within the individual 2D slices and discarded, reducing the accuracy of the resulting risk profile.

In an embodiment, at step 320, for each segmented 3D lesion, a set of statistics are calculated, such as 2D and 3D Agatston scores, volume, length, width, average HU value, maximum HU value, and the Euclidian distance to its corresponding arterial ostium. Compared to the conventional 2D Agatston score, which takes the maximum HU value in each 2D slice, the 3D Agatston score takes the maximum HU value in the whole 3D lesion or plaque volume. Therefore, theoretically, 3D Agatston score is more robust and reliable than 2D, because the 2D approach could be affected by changes in the orientation of the imaging plane/patient in highly inhomogeneous lesions.

After the statistics for the identified lesion are calculated, the process continues to step 316 to determine whether all ostia and lesions have been identified. If no, the process returns to step 310. If yes, then at step 322, the results of such calculations are saved to a storage device 110 and/or output as a report to the user. In an embodiment, the output is displayed on the user interface 108 or stored in the storage device 110.

Based on the lesion-specific quantification methodology 300 described herein, a prototype system and method was developed that has been successfully tested on CAC scans from two clinical CT scanners (Siemens Somatom 64-MSCT and Toshiba Aquilion ONE 320-MSCT). The methodology 300 can be adapted for use with a variety of models of CT scanners.

To facilitate use with multiple manufacturers' scanners, in an embodiment, the system 100 is adapted to parse and load in DICOM images with both DICOMDIR and XML structures. Alternative CAC volume image formats are adaptable to the LS-CAC systems and methods by one of ordinary skill in the art. Once the CAC volume is loaded, calcific regions are extracted using a HU threshold of 130. In an embodiment, this predefined threshold is user adjustable. For example, if the CAC volume is V, and x, y, and z are integral indexes in the X, Y and Z coordinates of the 3D volume, the binary calcific volume C can be derived by:

$$C(x, y, z) = \begin{cases} 1, & \text{if } V(x, y, z) \geq HU_{threshold} \\ 0, & \text{otherwise} \end{cases} \quad (1)$$

In an embodiment, the calcific volume is encoded with a color (e.g., red) and is overlaid on the gray-scale CAC images.

Figure 4A:
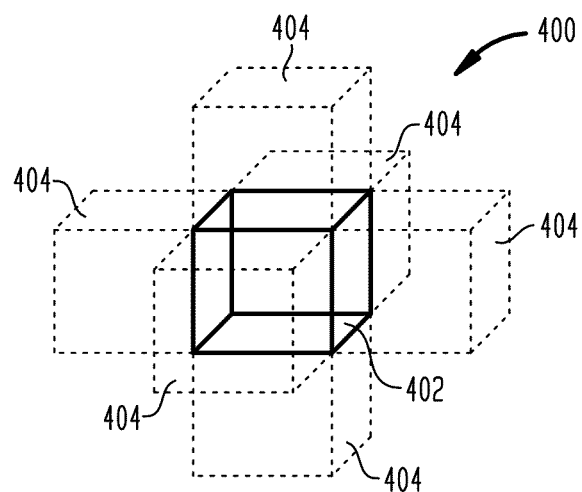
FIG. 4a depicts a model illustrating 6-connectiveness in a 3D volume.

Referring now to FIG. 4a, a model illustrating 6-connectiveness in 3D volumes is depicted. A central voxel 402 is surrounded by adjacent voxels 404, with an adjacent voxel 404 on each of its six sides. In an embodiment, during the flood-fill process, if the central voxel 402 is selected as a lesion point, each of these adjacent voxels 404 will be evaluated to determine whether they are part of the lesion as well.

Figure 4B:
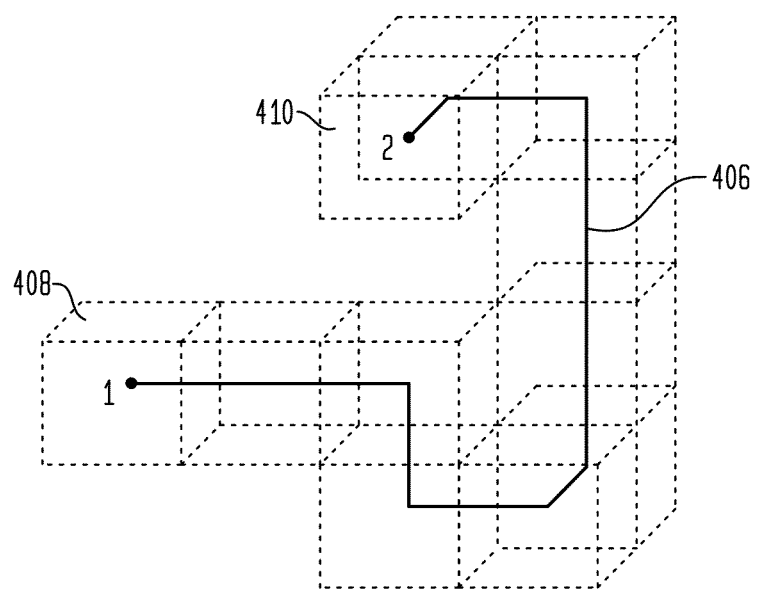
FIG. 4b depicts a model illustrating artifact mapping in a 3D volume utilizing 6-connectiveness.

FIG. 4b illustrates a path 406 connecting individual voxels, shown as a first voxel 408 and a second voxel 410, identified as part of a lesion. For two calcific voxels, such as the first voxel 408 and second voxel 410, voxels are 6-connected if they are 6-connected by a path 406 of calcific voxels. Accordingly, if the voxels along the path 406 are calcific voxels, the first voxel 408 is 6-connected with the second voxel 410.

In an embodiment, a 3D 6-connected flood-fill algorithm is adapted to segment the calcific lesion. There are many different implementations of the flood-fill operation known to those of ordinary skill in the art. One embodiment of a flood-fill method suitable for use with embodiments of the present system and method is detailed in Table 1.

TABLE 1

An exemplary 3D flood-fill algorithm.

1. Initialize an empty queue L to store the group of calcific voxels in the lesion of interest. Initialize an empty queue T.
2. If the seed point in the calcium volume $C(x_s, y_s, z_s) = 0$, return; Otherwise, add voxel $v_s = (x_s, y_s, z_s)$ to L and T.
3. While T is not empty, repeat the following steps:
    For each element $v = (x, y, z)$ of T, observe its 6 neighbors:
        If $C(x - 1, y, z) = 1$, and $v' = (x - 1, y, z) \notin L$: add v' to L and T.
        If $C(x + 1, y, z) = 1$, and $v' = (x + 1, y, z) \notin L$: add v' to L and T.
        If $C(x, y - 1, z) = 1$, and $v' = (x, y - 1, z) \notin L$: add v' to L and T.
        If $C(x, y + 1, z) = 1$, and $v' = (x, y + 1, z) \notin L$: add v' to L and T.
        If $C(x, y, z - 1) = 1$, and $v' = (x, y, z - 1) \notin L$: add v' to L and T.
        If $C(x, y, z + 1) = 1$, and $v' = (x, y, z + 1) \notin L$: add v' to L and T.
    Delete v from T.
4. Output L as the resulting calcific lesion.

Geometric and Morphologic Measurements

In embodiments, the length, width, volume, 2D/3D Agatston score, and the distance to its corresponding artery ostium of each segmented calcific lesion is measured after identification and mapping. Suppose lesion L contains N voxels: $v_i = (x_i, y_i, z_i) \in L$, i=1, 2, ... N, where $x_i, y_i, z_i$ are the integral indexes in the 3D volume. Suppose the voxel's resolution is $r = (r_x, r_y, r_z)$, which is specified in the DICOM image files. An individual voxel $v_i$'s physical coordinates can be obtained by: $p_i = (r_x \cdot x_i, r_y \cdot y_i, r_z \cdot z_i)$, i=1, 2, ... N. Suppose lesion L's corresponding artery ostium $O = (x_o, y_o, z_o)$. The physical coordinates of the ostium O can be derived as based upon the physical coordinates or position within the 3D volume and the resolution of individual voxels $r = (r_x, r_y, r_z)$ such that physical coordinates are derived as: $p_o = (r_x \cdot x_o, r_y \cdot y_o, r_z \cdot z_o)$.

The lesion's length and width is defined by calculating the lesion's thickness in the orthogonal directions along the lesion mass's first and third Eigen Vectors, described in further detail with respect to FIG. 5 below. Suppose $$\bar{p} = \frac{\sum_{i=1,2,\ldots N} p_i}{N}$$

is the center of mass of the lesion. We define the covariance matrix B as:

$$B = [p_1 - \bar{p}, p_2 - \bar{p}, p_N - \bar{p}] \cdot [p_1 - \bar{p}, p_2 - \bar{p}, p_N - \bar{p}]^T \quad (2)$$

Note that the dimension of B is 3×3. We apply principal component analysis on B and get the Eigen vectors $v_1$, $v_2$, $v_3$, and Eigen values, $\lambda_1$, $\lambda_2$, $\lambda_3$, respectively, and $\lambda_1 \geq \lambda_2 \geq \lambda_3$.

Figure 5:
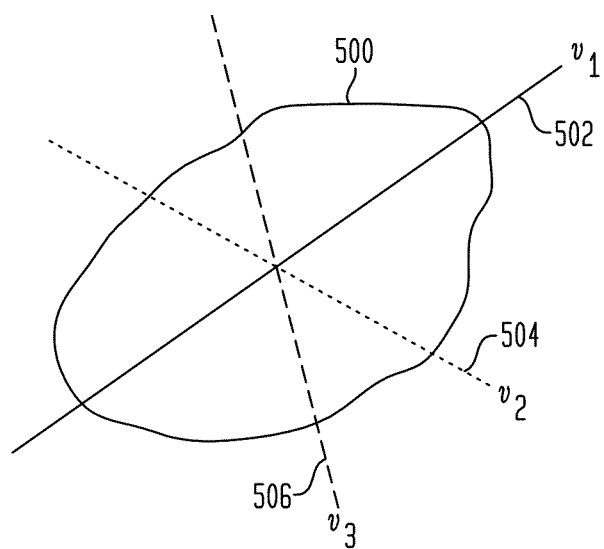
FIG. 5 is an example of segmented 3D calcific lesion, and the measurement of the lesion's length and width.

FIG. 5 is an example of a segmented 3D calcific lesion 500. Eigen vectors, v1, v2 and v3, 502-506, associated with the lesion 500 are depicted. In an embodiment, the processor 106 calculates a set of statistics relevant to the risk profile of the lesion, based upon the geometry and location of the lesion 500. In an embodiment, the length, width, volume, 2D and 3D Agatston score, as well as the distance to its corresponding artery ostium (not shown) of each segmented calcific lesion 500 are computed.

In an embodiment, an ellipsoid shape is assumed or used as an initial model of a lesion to determine Eigen vector 502, 504 and 506 axes. The longest axis can be assumed to be oriented parallel with the artery, due to the nature of lesion growth patterns. In an embodiment, the assumption of ellipsoid shape is utilized to determine the orientation of the Eigen vectors 502, 504, and 506. In another embodiment, length of the lesion is determined based upon the first Eigen vector 502. In a further embodiment, width is determined based upon the extent of the lesion along the direction of the axis of the third Eigen vector 506, but because lesions are often irregularly shaped, the width is not assumed to be greatest on the Eigen vector 506 itself. In this embodiment, the maximal width in the direction of the third Eigen vector 506 along the length of the first Eigen vector 502 is considered the width of the lesion, and indicates the protrusion of the lesion into the ostium of the artery, as described further with respect to FIG. 6.

As discussed above, each representation of a lesion 500 contains N voxels, or a certain quantity of 3D data, $v_i = (x_i, y_i, z_i) \in L$, $i = 1, 2, \ldots N$, where $x_i$, $y_i$, $z_i$ are the integral indexes in the 3D volume of N. Accordingly, the position of a given lesion voxel, i, within the matrix defined by the 3D volume is defined by the coordinates $x_i$, $y_i$, $z_i$, also referred to herein as the position coordinates. The voxel's resolution, or relationship of the voxel to real world distance measurements can be represented as $r = (r_x, r_y, r_z)$. The voxel's physical coordinates within the physical world can then be obtained by the dot product of the voxel position coordinates and the resolution of the voxel: $p_i = (r_x \cdot x_i, r_y \cdot y_i, r_z \cdot z_i) = 1, 2, \ldots N$. The lesion's corresponding artery ostium, $O = (x_o, y_o, z_o)$, can then be located by deriving: $p_o = (r_x \cdot x_o, r_y \cdot y_o, r_z \cdot z_o)$, where $x_o, y_o, z_o$ are the position coordinates of the artery ostium voxel and the voxel's resolution is represented as $r = (r_x, r_y, r_z)$.

In an embodiment, the lesion's length and width is defined by calculating the lesion's thickness in the orthogonal directions along the lesion mass's first 502 and third 506 Eigen vectors. Lesion's length, as determined along the first Eigen vector 502, is defined as the maximum distance between any two lesion voxels along the direction of the first Eigen vector 502 $v_1$:

$$L = \max_{i=1,2,\ldots N, j=1,2,\ldots N, i\neq j} |(p_i - p_j)^T \cdot v_1| \quad (3)$$

The width 506 of the lesion is defined as the maximum distance between any two lesion voxels along the direction of the third Eigen vector 506 $v_3$:

$$W = \max_{i=1,2,\ldots N, j=1,2,\ldots N, i\neq j} |(p_i - p_j)^T \cdot v_3| \quad (4)$$

The lesion's volume is defined as the number of voxels within the lesion N, multiplied by the resolution of the voxel:

$$Vol = N \cdot r_x \cdot r_y \cdot r_z \quad (5)$$

To remove noise in conventional Agatston scores, 2D calcific lesions in a single 2D slice, where lesions with an area smaller than 1 mm² are treated as noise, and can be discarded. As discussed above, where a lesion is narrow but long, if the axis of the lesion is oriented in the same direction as the stack of 2D slices, a lesion may appear to be less than 1 mm² in each individual slice. Accordingly, a lesion of significant size overall may be eliminated as noise from the set of 2D slices since it fails to appear as larger the noise threshold in the individual 2D slices.

In embodiments of the LS-CAC systems and methods, this de-noising strategy of conventional 2D systems is adapted for 3D processing. In an embodiment, calcific lesions are evaluated as volumes, such that if the 3D volume of a lesion is smaller than a defined noise threshold, e.g., 1 mm³, the lesion is treated as noise, and be discarded. Because the volume of the lesion is evaluated, this particular embodiment would retain the data regarding the long, narrow lesion that would have been discarded in the 2D conventional system. In another embodiment, according to the imaging quality, users can also actively adjust the noise threshold. In a further embodiment, the LS-CAC system 100 can utilize conventional 2D Agatston scores, as well as 3D Agatston scores.

In an embodiment, the 3D Agatston scoring method is similar to the conventional 2D method for Agatston scoring, except that the whole 3D volume and the highest HU value in the whole 3D lesion are used as opposed to calculating 2D Agatston scores for each individual 2D slice of the 3D volume and then summing the 2D Agatston scores for each slice.

The distance to the ostium is defined as:

$$D = |p_o - \bar{p}|_2 \quad (6)$$

where $p_o$ is the position of the ostium within the 3D volume and p is the position of the lesion within the 3D volume.

The lesion's maximum HU value is defined as:

$$HU_{max} = \max_{i=1,2,\ldots,N} C(x_i, y_i, z_i) \quad (7)$$

The lesion's average HU value is defined as:

$$HU_{mean} = \sum_{i=1,2,\ldots,N} C(x_i, y_i, z_i)/N \quad (8)$$

In an embodiment, the LS-CAC system 100 computes a detailed set of statistics or measurements regarding each lesion within the CAC volume. For example, the system 100 computes lesion level measurements including, but not limited to, Lesion Volume, Lesion Agatston Score, Lesion 3D Agatston Score, Lesion Length, Lesion Width, Distance to corresponding vessel's ostium, Maximum HU and Mean HU. In addition, the system 100 can compute statistics and measurements associated with each of the four major arteries. These vessel level measurements include, but are not limited to, Lesion Number, Total Volume, Total Agatston Score, Total 3D Agatston Score, Maximum Lesion Volume, Maximum Lesion Agatston Score, Maximum Lesion 3D Agatston Score, Maximum Lesion Length, Maximum Lesion Width, Mean Lesion Volume, Mean Lesion Agatston Score, Mean Lesion 3D Agatston Score, Mean Lesion Length, Mean Lesion Width, Shortest Distance to corresponding vessel's ostium, and Largest lesion's (with maximum Agatston Score) distance to corresponding vessel's ostium. In a further embodiment, the system 100 computes whole heart level measurements including, but not limited to, Total Lesion Number, Whole Heart Volume Score, Whole Heart Agatston Score, and whole Heart 3D Agatston Score.

Figure 6:
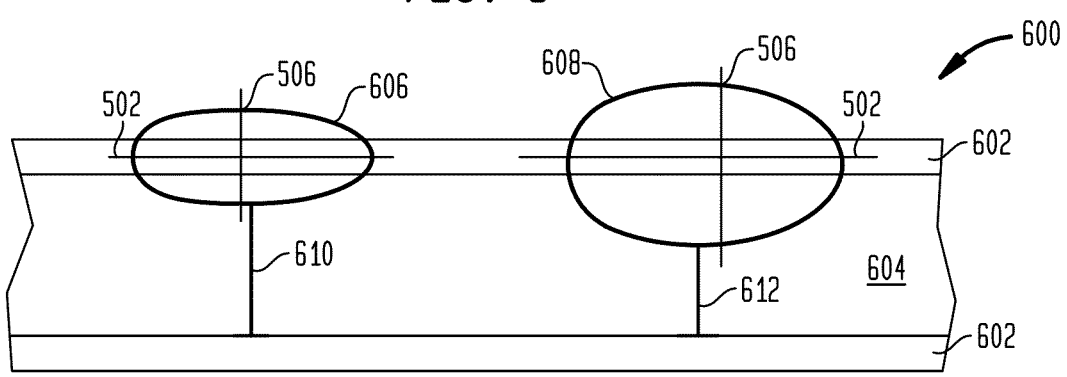
FIG. 6 illustrates an exemplary cross-section of an artery with lesions of varying geometries.

FIG. 6 illustrates a cross section of an artery 600, including the artery walls 602 and ostium 604. The illustrated artery 600 has a first lesion 606 and a second lesion 608 of varying geometries. As shown, second lesion 608 is slightly larger than the first lesion 606 and protrudes further into the ostium 604 of artery 600. The first Eigen vector 502 of each of the first lesion 606 and second lesion 608 is generally oriented substantially parallel with the artery wall 602. This is typical lesion geometry.

In an embodiment of the LS-CAC system 100, conventional statistics such as total 2D Agatston and over-all CAC volume scores are computed for the CAC volume. In addition, lesion-specific statistics or measurements, including lesion geometry data, are computed. For example, the LS-CAC system 100 computes a 2D and 3D Agatston score, volume score, length, width, average maximum attenuation values in Hounsfield (HU), and the distance from corresponding artery ostium 604 for each of the first lesion 606 and second lesion 608. These statistics can be maintained in the storage device 110. These lesion specific measurements highly correlate with the instances of coronary artery stenosis, and plaque volumes and compositions.

In an embodiment, a lesion-specific volume, 2D and 3D Agatston score for each lesion is measured along with its distance from the corresponding coronary ostia 604. A first distance 610 is indicative of the distance that the first lesion 610 extends into the ostium 604 and the portion of the ostium 604 that remains unobstructed by the first lesion 606. A second distance 612 is indicative of the distance that the second lesion 612 extends into the ostium 604 of the artery 600, and the portion of the ostium 604 that remains unobstructed by the second lesion 608. This measure of obstruction by lesions is highly indicative of the risk posed by individual lesions. This information can serve as a model to evaluate the overall event risk by combining the risks from all the lesions using a Naïve Bayesian technique, which assumes that the event risk caused by each lesion is independent to each other.

Figure 7:
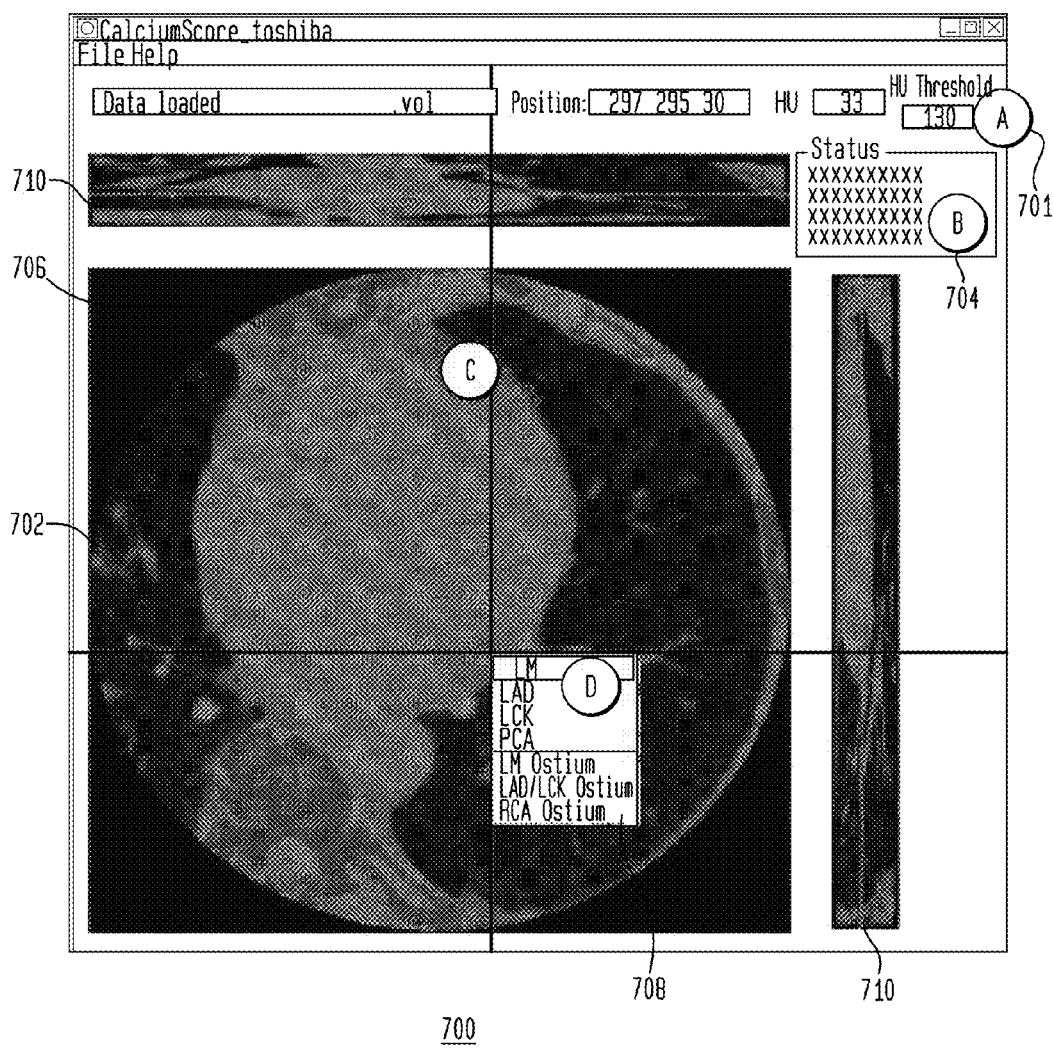
FIG. 7 is an example of a graphical user interface allowing a physician to interact with the systems and methods described herein.

Referring now to FIG. 7, an embodiment of a graphical user interface 700 for a system 100 that performs lesion-specific CAC quantification is illustrated. The depicted graphical user interface 700 is one possible embodiment of the user interface 108 of the LS-CAC system 100. In an embodiment, the user interface 700 includes an editable field 701 (A) of the HU threshold of calcific regions. In a further embodiment, the graphical user interface 700 includes a view or window 702 (C) that displays the binary calcium volume. In an alternate embodiment, the binary calcium volume is displayed in gray-scale, where intensity of the pixels indicates the density of calcium at a particular location. Areas identified as lesions can be indicated using color to allow users to easily recognize lesions. For example, an annotated calcific lesion 706 appears as a shaded region to indicate a lesion in the LAD artery. In a further embodiment, the user interface 108 includes a mouse, trackball or other control device that allows the user to scroll through the binary calcium volume and select one or more points.

In other embodiments, the graphical user interface 700 includes a status panel 704 (B) that allows users to label three arterial ostia. Users can select individual points within the binary calcium volume utilizing the window 702 and a control device, such as a mouse to select a point. In a further embodiment, upon selection of a point, the user can right-click with a mouse, or otherwise use a control device to initiate a popup menu 708 (D), which allows for the classification of specific regions of the calcific volume 702.

In an embodiment, the graphical user interface 700 allows users to easily browse through the entire 3D CAC volume. By interactively clicking on the GUI's three orthogonal cross-section views, users are able to localize and annotate the four major coronary arteries' ostia, i.e., left main (LM) ostium, left anterior descending (LAD) and left circumflex (LCx) ostium, and right coronary artery (RCA) ostium.

By clicking and specifying a seed point within each coronary calcific lesion, users can interactively localize calcific lesions and annotate their corresponding arteries, i.e., LM, LAD, LCx, and RCA. For lesions that cover two or more arteries, their corresponding artery is defined as the artery that is more proximal. For example, if a lesion locates at the ostium of LAD and LCx, and covers all three LM, LAD and LCx arteries, the lesion is labeled as LM.

In an embodiment, from the user-specified seed point, a 3D 6-connected flood-fill operation is applied to segment the 3D calcific lesion. This 3D flood-fill operation automatically propagates through the 3D CAC volume using a 6-connectiveness criterion. Accordingly, users are not required to label the lesion slice by slice, as in required in the conventional 2D methodology, in which the CAC volume is represented as a stack of 2D slices. In this manner, the described method can vastly expedite the image analysis process. Another advantage of the described 3D approach is that the de-noising method using volume-size-thresholding in 3D is more accurate than in 2D. In conventional 2D approaches, for de-noising purposes, lesions in a single 2D slice with volume size smaller than 1 $mm^3$ are treated as noise and discarded. However, this is may be inaccurate, since these small-sized 2D lesions could be parts of larger 3D lesions, as discussed in detail above.

In an embodiment, for each segmented 3D lesion identified by the user, 2D and 3D Agatston scores, volume, length, width, average HU value, maximum HU value, and the Euclidian distance are calculated to its corresponding arterial ostium. Compared to the conventional 2D Agatston score, which takes the maximum HU value in each 2D slice, 3D Agatston score takes the maximum HU value in the whole 3D plaque volume. Therefore, theoretically, 3D Agatston score is more robust and reliable than 2D, because the 2D approach could be affected by changes in the orientation of the imaging plane/patient in highly inhomogeneous plaques.

In the embodiment illustrated in FIG. 2, the graphical user interface 700 allows the user to freely browse through the 3D volume by interactively clicking on the three orthogonal cross-section views, including the window 702 and additional displays of 3D image data 710. In an embodiment, users can save the resulting data, describing the location and geometry of one or more lesions, to a storage device 110.

FIG. 8 depicts an exemplary lesion specific CAC quantification report 800, which presents traditional measures such as total Agatston and volume scores as well as enhanced information, such as each lesion's 3D Agatston score, volume score, length, width, average and maximum attenuation values in Hounsfield unit (HU), and the distance of each lesion from corresponding vessel's ostium. In an embodiment, each segmented 3D lesion, 2D/3D Agatston score, volume, length, width, average HU value, maximum HU value, and the Euclidian distance are calculated to its corresponding arterial ostium. The 3D Agatston score takes the maximum HU value in the whole 3D plaque volume. These lesion-specific measurements highly correlate with the instances of coronary artery stenosis, and plaque volumes and compositions. The results provide a comprehensive report that describes risk profile rather than basic output from existing 2D systems. Using a Naïve Bayesian approach, a distance-weighted measurement of the lesion-specific CAC was developed, which is more predictive of cardiovascular events compared to the overall CAC scores.

Clinical Applications and Results

Laboratory testing data was used to demonstrate that vessel-specific and lesion-specific coronary artery calcium scores generated by the method/process described above and implemented using the described systems and methods, but not total Agatston or volume scores, are accurate in predicting obstructive coronary artery stenosis. In this study, 100 patients with CAC and invasive angiography (XRA) data were investigated. Vessel-specific CAC was determined for each major artery, i.e., the left main, the left anterior descending, and the right coronary artery. Average lesion-specific score was calculated by dividing the vessel-specific score by the number of lesions within the corresponding vessel. Coronary artery stenosis greater than 50% on XRA was used as the criterion to label the corresponding vessel with obstructive CAD. It was noted that the Agatston and volume scores were similar in patients with/without obstructive CAD (335.8±74.1, vs. 652.4±186.5; p=0.13 and 299.5±61.4 vs. 539.9±147.9; p=0.14). In contrast, vessel-specific score, vessel-specific volume, average lesion-specific score and average lesion-specific volume were significantly different between patients with/without obstructive CAD (77.8±12.1 vs. 309.5±65.2, p=0.001; 69.3±10.1 vs. 252.9±50.9, p=0.001; 22.5±3.1 vs. 69.8±15.0, p=0.004 and 20.3±2.6 vs. 57.6±11.6, p=0.003). As shown in Table 2, ROC analysis also showed superiority of vessel- and lesion-specific scores over the total Agatston and volume score.

TABLE 2

ROC analysis of the vessel-specific/lesion-specific CAC scores and total scores with respect to vessel stenosis.

|  | Optimal Cupoint | AUC | Standard deviation | 95% confidence interval | p-value | Sensitivity | Specificity |
| --- | --- | --- | --- | --- | --- | --- | --- |
| Vessel-specific score | 28.9 | 0.789 | 0.0479 | 0.724-0.844 | 0.0001 | 88.6 | 59.9 |
| Vessel-specific volume | 24.2 | 0.786 | 0.0481 | 0.721-0.842 | 0.0001 | 91.4 | 58.0 |
| Average lesion-specific score | 12.5 | 0.761 | 0.0498 | 0.694-0.820 | 0.0001 | 82.9 | 59.9 |
| Average lesion-specific volume | 11.8 | 0.762 | 0.0497 | 0.696-0.821 | 0.0001 | 85.7 | 58.6 |
| Total Agatston score | 594.5 | 0.584 | 0.0834 | 0.433-0.724 | 0.3145 | 36.4 | 84.6 |
| Total volume | 580.6 | 0.582 | 0.0835 | 0.431-0.723 | 0.3250 | 36.4 | 88.5 |

In another study, the total CAC scores with lesion-specific calcium quantification were compared by validating against intravascular ultrasound (IVUS) virtual histology (VH) with radiofrequency analysis. It was demonstrated that lesion-specific measures correlate with values of lumen stenosis and plaque composition by virtual histology (VH), while total CAC scores only correlate with the overall plaque burden on IVUS. In this study, 24 patients with CAC, IVUS/VH and Framingham Risk Score (FRS) were investigated. On CAC scans, the total Agatston and volume scores (AS, VS) were determined. Each lesion was scored individually and determined lesion-specific AS, lesion-specific VS, width and length. Minimal lumen diameter (MLD) and area (MLA), percent atheroma volume (PAV) and percent area stenosis (% AS) were measured on IVUS. Fibrous (FI), fibrofatty (FF), necrotic core (NC) and dense calcium (DC) volume and percent were measured on VH. The correlation coefficients r and p value were calculated. A value of p<0.05 was considered significant. It was found that the Framingham Risk Score (FRS) was not predictive of IVUS/VH parameters. As shown in Table 3, it was found that the whole-heart 2D and 3D Agatston and volume score significantly correlated with the overall percent atheroma volume on IVUS, but not with measures of lumen stenosis. However, lesion-specific measures correlated with minimal lumen diameter and percent area stenosis; such measures also correlated with percent atheroma volume. Furthermore, whole-heart measures did not correlate with VH parameters, except volume score vs. fibrofatty percentage. However, several lesion-specific values correlated with necrotic core and dense calcium volume.

TABLE 3

Comparison of whole-heart and lesion-specific calcium quantifications by validating against IVUS/VH parameters.
Whole-Heart and Lesion-Specific CAC vs IVUS/VH Parameters

|  | CAC | IVUS/VH | r-value | p-value |
| --- | --- | --- | --- | --- |
| Whole-Heart Score | Agatston | PAV | 0.6059 | 0.0046 |
|  | Volume Score | PAV | 0.5869 | 0.0065 |
| Lesion-Specific Score | Lesion Width | MLD | −0.5490 | 0.0122 |
|  | Lesion Length | PAV | 0.4376 | 0.0325 |
|  | Agatston | % AS | −0.4780 | 0.0330 |
|  | Lesion Width | % AS | −0.4641 | 0.0393 |
|  | Volume | % AS | −0.5041 | 0.0234 |
|  | Volume | DC Volume | 0.5463 | 0.0057 |
|  | Volume | NC Volume | 0.4071 | 0.0483 |

Only significant correlations are listed.

Another study tested the hypothesis that DWLS-CAC is more predictive of cardiovascular events than the whole-heart Agatston score. This study demonstrated that distance-weighted lesion-specific evaluation of CAC is more predictive of cardiovascular events compared to the total Agatston and volume scores. In this study, 30 patients (10 with events and 20 without events) were investigated. Their total AS and VS. Lesion-specific were measured. VS and AS were also measured for each lesion and its distance from the corresponding coronary ostia. A model was developed to predict risk of each lesion based on its lesion-specific AS/VS and its distance from the ostium, assuming a sigmoid-shaped increasing relationship between risk and lesion-specific AS/VS and a sigmoid-shaped decreasing relationship between risk and distance, where the sigmoid shapes were modeled by single-sided Gaussian curves.

Suppose the event probability caused by a lesion i is $p_i$, which is a function of its lesion-specific AS/VS $s_i$ and its distance to the ostium d $$p_i = \begin{cases} a_i \cdot \exp\left(\frac{-d_i^2}{2\sigma_d^2}\right), & \text{if } s_i > 3\sigma_s \\ a_i \cdot \exp\left(\frac{-d_i^2}{2\sigma_d^2}\right) \cdot \exp\left(\frac{-(s_i - 3\sigma_s)^2}{2\sigma_s^2}\right), & \text{if } s_i \leq 3\sigma_s \end{cases} \quad (9)$$

where a is a coefficient, $\sigma_d$ and $\sigma_s$ are the Gaussian standard deviations of the AS/VS and distance sigmoid-shaped models. A model was developed to evaluate the overall event risk by combining the risks from all the lesions using a Naïve Bayesian technique, which assumes that the event risk caused by each lesion is independent to each other. Therefore, the overall event probability P can be derived by:

$$P = 1 - \prod_{i=1,2,\ldots,N} (1 - p_i) \quad (10)$$

P where $p_i$ is the event risk (probability) caused by lesion i and N is the total number of calcific lesions presented in the heart. P should be optimized by tuning parameters a, $\sigma_d$ and $\sigma_s$ to achieve the smallest p-value between patients with/without events using an unpaired t-test.

For the 30 CAC positive scans, we calculated their overall event risk Pk; (k=1; 2 . . . 30) using Equations 9 and 10.

$$t = \frac{\overline{P}_{event} - \overline{P}_{no\_event}}{\sqrt{\frac{s_{event}^2}{10} + \frac{s_{no\_event}^2}{20}}} \quad (11)$$

$$v = \frac{(s_{event}^2/10 + s_{no\_event}^2/20)^2}{(s_{event}^2/10)^2/9 + (s_{no\_event}^2/20)^2/19} \quad (12)$$

$$\{a_i, \sigma_s, \sigma_d^{LAD}, \sigma_d^{LCx}, \sigma_d^{RCA}\} = \underset{a_i,\sigma_s,\sigma_d^{LAD},\sigma_d^{LCz},\sigma_d^{RCA}}{\arg\min} B\left(\frac{v}{v+t^2}, \frac{v}{2}, \frac{1}{2}\right) \quad (13)$$

where $\overline{P}_{event}$ and $\overline{P}_{no\_event}$ are the means of the $P_k$s of the 10 patients with cardiac events and the 20 patients without event, respectively, and similarly, $s^2_{event}$ and $s^2_{no\_event}$ are $P_k$s' standard deviations. B is the incomplete beta function. The optimization is implemented through a brutal force approach with multiple resolutions and a local gradient-descent refinement step, which make the convergence faster.

Utilizing a lesion-specific CAC quantification system and the event risk model, the optimized overall distance-weighted lesion-specific Agatston score and volume score (DWLS-AS/DWLS-VS) was derived from the 30 CAC scans. The Framingham Risk Score (FRS), AS, VS, maximum lesion AS/VS were compared in each vessel and distance weighted lesion-specific AS/VS between patients with/without events using unpaired t-test and ROC analysis. As shown in Table 4, FRS, total AS/VS, and maximum lesion AS/VS were similar in patients with and without events. However, distance weighted lesion-specific AS/VS Ps were significantly different (0.1078±0.055 vs. 0.0607±0.043; p=0.03 and 0.1085±0.055 vs. 0.0611±0.044; p=0.03).

Distance from ostium was more important in LCx and RCA compared to LAD ($3\sigma_d$: 33 mm, 30 mm, >100 mm, respectively). The conclusion was drawn that more proximal calcified lesions have higher risk of cardiac events; therefore, distance-weighted lesion-specific evaluation of standard CAC scans significantly improves predictive value. Such evaluation can be easily implemented in clinical practice by using the lesion-specific calcium quantification framework described herein.

TABLE 4

Statistics of different calcium quantification measures in patients with/without event.

| | Mean ± SD (Event vs. No Event) | p-Value | AUC |
|---|---|---|---|
| Total Volume Score | 683.8 ± 642.3 vs. 480.0 ± 628.0 | 0.4201 | 0.66 |
| Total Agatston Score | 826.5 ± 819.2 vs. 539.8 ± 687.1 | 0.3553 | 0.64 |
| Framinghan Risk Score | 6.44 ± 4.61 vs. 6.30 ± 4.89 | 0.9399 | 0.50 |
| Maximum Volume Score | 333.1 ± 354.8 vs. 226.5 ± 316.8 | 0.4335 | 0.64 |
| Maximum Agatston Score | 433.3 ± 471.9 vs. 301.8 ± 415.9 | 0.4687 | 0.64 |
| Distance weighted Lesion-Specific Volume Score | 0.1085 ± 0.055 vs. 0.0611 ± 0.044 | 0.0315 | 0.75 |
| Distance weighted Lesion-Specific Agatston Score | 0.1078 ± 0.055 vs. 0.0607 ± 0.043 | 0.0317 | 0.75 |

Distance weighted lesion-specific scores (highlighted) are significantly different (p = 0.03) in patients with/without event, which could be of event-predictive value.

Figure 9:
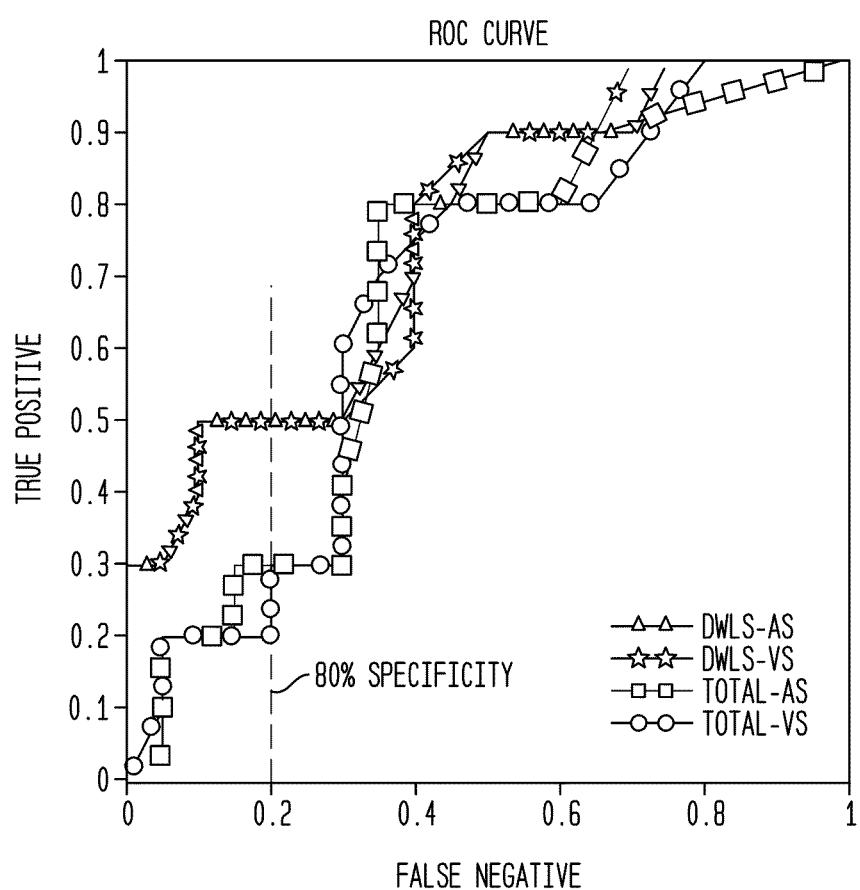
FIG. 9 illustrates ROC curves of whole-heart, vessel- and lesion-specific CAC scores.

As shown in FIG. 9, the areas under the ROC curve (AUC) of DWLS and AS/VS were both 75%, which are significantly larger than the AUC of total-AS/VS, which were 64% and 66%. At the specificity point of 80%, which is commonly used as the clinical cutpoint for choosing interventional treatment, the sensitivity of the DWLS-AS/VS measurements are 20%±30% higher than the whole-heart scores.

TABLE 5

The $\sigma_d$ and $\sigma_s$ values of DWLS-AS/VS.

| | $\sigma_s$ | $\sigma_d^{LAD}$ | $\sigma_d^{LCx}$ | $\sigma_d^{RCA}$ | $a_i$ |
|---|---|---|---|---|---|
| DWLS-AS | 3030 | >100 cm | 12.6 mm | 10.1 mm | 1 |
| DWLS-VS | 2301 | >100 cm | 12.1 mm | 10.0 mm | 1 |

In Table 5, the parameters derived from the optimization process of the DWLS-AS/VS models are listed. The more proximal calcified lesions have higher marginal risks of cardiac events in LCx and RCA, where $\sigma_d^{LCx}$=12.6 mm in DWLS-AS, $\sigma_d^{LCx}$=12.1 mm in DWLS-VS, $\sigma_d^{RCA}$=10.1 mm in DWLS-AS and $\sigma_d^{RCA}$=10.0 mm in DWLS-VS. Suppose that 36 is the cutoff point of the Gaussian model, then most of the culprit lesions locate within the proximal 3 to 4 cm segments of the LCx and RCA, which is in good accord with clinical observations. For LAD, we observe that $\sigma_d^{LAD}$ s of DWLS-AS/VS are both >100 cm, which shows that lesions in LAD have the same high marginal event probability as in LM, in regard of their geometric locations. This is in accord with clinical observations as well: LAD is a more important major coronary artery that supplies the largest cardiac territory; physicians tend to choose revascularization treatment, which is one instantiation of MACE, for LAD atherosclerosis, even if the plaque location is relatively dismal. $\sigma_s$ is the standard deviation of the AS/VS scores.

Figure 11:
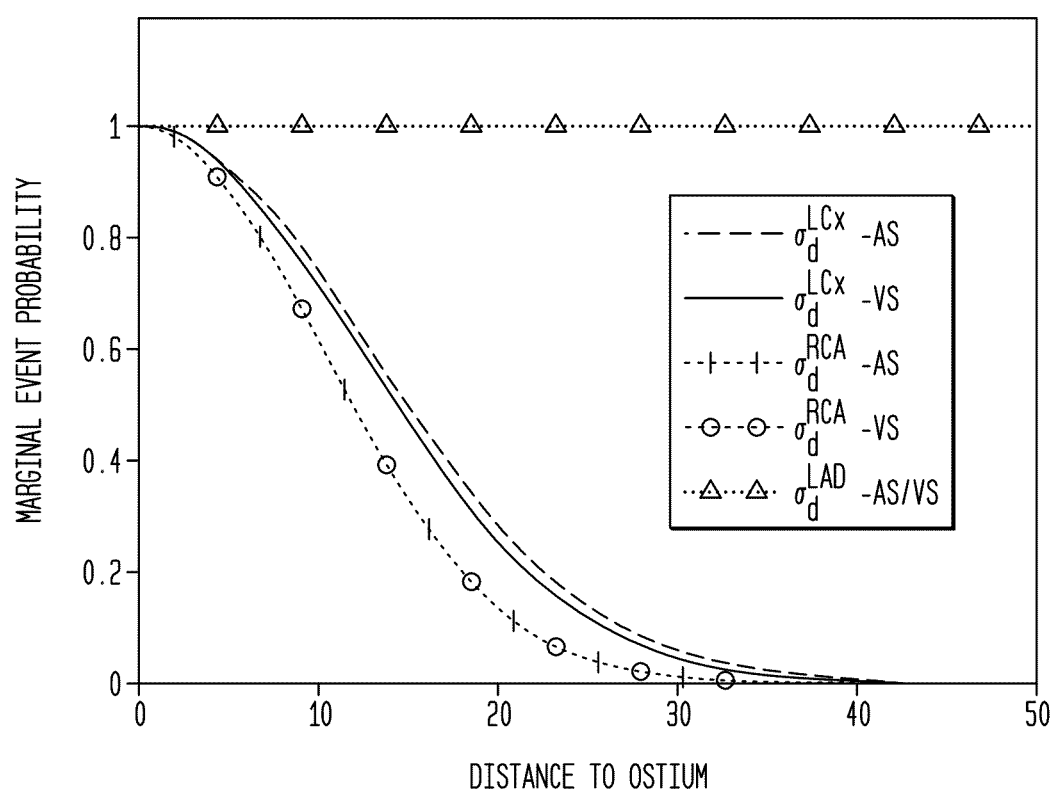
FIG. 11 depicts an exemplary graph of marginal event probability based upon distance of a calcific lesion from the ostium of an artery.
Figure 12:
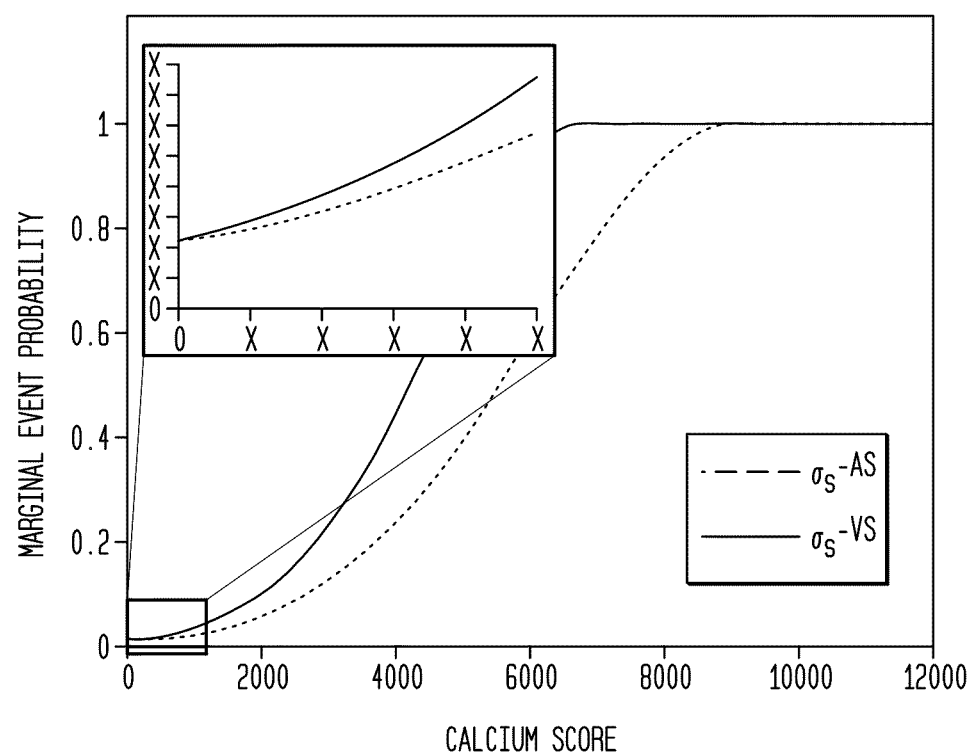
FIG. 12 depicts an exemplary graph of marginal event probability based upon calcium score of a calcific lesion.

As shown in FIGS. 11 and 12, $\sigma_{s\text{-}As}$ is larger than $\sigma_{s\text{-}As'}$, since AS is usually larger than VS. FIGS. 11 and 12 illustrate marginal probabilities versus $\sigma_d$, for FIG. 11, and $\sigma_s$, for FIG. 12, curve of DWLS-AS/VS. It is also interesting to observe that in the single-lesion AS/VS ranges of 0~1000, which are most common in clinical CAC scans, the marginal risk probability and the AS/VS score have an approximate linear relationship, which agrees with the findings in whole-heart CAC AS/VS studies.

In a retrospective, single-center, observational study; 91 consecutive patients referred to the Piedmont Heart Institute between January 2005 and June 2006 for both coronary artery calcium scoring and invasive X-ray coronary angiography within 12 months were included. This study was designed to investigate the diagnostic accuracy of different CAC measurements for obstructive CAD in patients with positive CAC; those with negative calcium scores were excluded (7 patients). Enrollment criteria were met by 84 patients. Demographic and clinical information was collected from medical records.

CAC examinations were performed on a 32×2 multi-detector (MDCT) system (Siemens Somatom 64; Erlangen, Germany). Non-contrast CAC scans were performed during end-respiratory breath hold with retrospective electrocardiographic (ECG)-gating. CAC images were acquired using 3 mm collimation with a 2 mm inter-slice gap. Other acquisition parameters included a gantry rotation of 375 ms, pitch 0.24, tube voltage 120 kV and tube current of 250 mAs.

Invasive X-ray coronary angiography was performed by using the Judkins technique based on institutional protocols, acquiring a minimum of five views of the left coronary system and two views of the right coronary system. The absence or presence of discrete coronary artery stenoses was examined in two orthogonal views and obstructive disease was confirmed by visual assessment. Two criteria for obstructive CAD, ≥50% diameter stenosis and ≥70% diameter stenosis, were used. The coronary vasculature was divided into 4 territories, i.e., left main coronary artery (LMCA), left anterior descending artery (LAD), left circumflex artery (LCx), and right coronary artery (RCA). Presence of obstructive CAD was recorded for each corresponding vessel.

Total Agatston score was calculated by standard methods. The area of calcification was multiplied by an arbitrary weighted density score based on the maximum Hounsfield unit (HU) value in the identified 2D calcified lesion, as follows: 1=130-199 HU; 2=200-299 HU; 3=300-399 HU; 4=400 HU and above. Calcium scores in all 2D calcified lesions along the major epicardial arteries were summed to derive the whole-heart Agatston score. Volume score was calculated as the total volume of the calcification in the major epicardial arteries, where calcification was identified as voxels with attenuation values equal to or greater than 130 HU. Lesion-specific Agatston and volume scores were measured in each single calcified lesion. A single calcified lesion was defined as a complete group of connected calcified voxels based on the 6-connectedness criterion in 3D. A software system has been developed to allow users to manually annotate calcified lesions followed by automated lesion segmentation. Vessel-specific CAC was determined as the sum of the lesion-specific CAC scores in the corresponding vessel. Lesions that covered two or more vessels were divided according to their locations. The maximum lesion-specific CAC was specifically recorded and the mean lesion-specific CAC in each vessel was calculated (vessel-specific score divided by the number of individual lesions).

Since patients with negative CAC scores were excluded in the study cohort, in order to achieve comparable sample distribution, only vessels with positive CAC scores were investigated in the vessel/lesion-specific CAC study. Normal vs. non-normal distribution was assessed by the Kolmogorov-Smirnov test. Normally distributed continuous variables were compared by unpaired two-tailed t-test. Non-normally distributed values were compared by independent Mann-Whitney test. Receiver operating characteristics (ROC) curves and the area under the curve (AUC) were used to evaluate and compare the diagnostic performance of different CAC parameters in diagnosing obstructive CAD. ROC cut-points were also selected to achieve 80% specificity or sensitivity, and the corresponding positive predictive value (PPV), negative predictive value (NPV), and sensitivity/specificity were compared between the whole-heart and vessel/lesion-specific approaches. Statistical significance was determined by a p-value <0.05.

Results

Overall Patient Characteristics

Of the 91 patients screened, 84 met enrollment criteria with positive CAC results. Mean age was 66.1±8.5; 52 (61.2%) of patients were male. Clinical factors were not different between patients with and without obstructive CAD by either definition (≥50% or ≥70% diameter stenosis) (Table 6).

TABLE 6

Demographic data.

|  | No. of Patients | No. of <50% Stenosis | No. of ≥50% Stenosis | No. of ≥70% Stenosis |
|---|---|---|---|---|
| All | 84 | 27 (32%) | 57 (68%) | 33 (39%) |
| Male | 52 (62%) | 14 (27%) | 38 (73%) | 22 (42%) |
| Female | 32 (38%) | 13 (41%) | 19 (59%) | 11 (34%) |
| Mean age ± SD(yrs) | 66.1 ± 8.5 | 65.3 ± 10.0 | 66.6 ± 7.8 | 65.8 ± 8.2 |

SD: standard deviation; No: number. Age distribution was similar in patients with and without obstructive CAD by X-ray angiography using unpaired Welch-tests, with p = 0.55 (based on ≥50% diameter stenosis) and 0.74 (based on ≥70% diameter stenosis). Gender distribution was similar in patients with and without obstructive CAD by X-ray angiography based on frequency table analysis and $\chi^2$ tests, with p = 0.29 (based on ≥50% diameter stenosis) and 0.62 (based on ≥70% diameter stenosis).

Coronary Artery Disease by Invasive Coronary Angiography 242 calcium positive coronary vessels were evaluated, including 38 LMCA, 79 LAD, 68 LCx, and 57 RCA, in 84 patients. Based on a criterion of ≥50% stenosis, 57 out of 84 patients (67.9%) and 83 out of 242 vessels (34.3%) had obstructive CAD (1 LMCA, 47 LAD, 17 LCx, and 18 RCA); based on a criterion of ≥70% stenosis, 33 out of 84 patients (39.3%) and 36 out of 242 vessels (14.9%) had obstructive CAD (15 LAD, 11 LCx, and 10 RCA).

Whole-Heart CAC Scores, Vessel-Specific and Lesion-Specific CAC Scores

CAC scores were non-normally distributed in the overall study population (Kolmogorov-Smirnov test for normal distribution: p=0.001); mean(±SD) whole heart Agatston score was 641(±709), median was 400. Mean(±SD) whole-heart volume score was 536(±570); median was 338. Using a criterion of ≥50% stenosis for obstructive CAD by XRA, whole-heart Agatston score and volume score were not significantly different between patients with and without obstructive CAD (median [interquartile range]: 436 [95,1177] vs 309 [84,574], p=0.23; and 374 [108,988] vs 265 [76,480], p=0.18, respectively). However, vessel-specific and lesion-specific values were significantly higher in patients with obstructive CAD (maximum lesion specific Agatston score: 165 [53,294] vs 47 [15,110]; p<0.0001).

Diagnostic Characteristics of Whole-Heart, Vessel- and Lesion-Specific CAC Scores by ROC Analysis ROC curves of whole-heart, vessel- and lesion-specific CAC scores in predicting ≥50% and ≥70% obstructive CAD are shown in FIG. 9; corresponding optimal cut-points with corresponding sensitivity, specificity, positive predictive value (PPV) and negative predictive value (NPV) are shown in FIG. 10. For the prediction of 50% stenosis by XRA, all vessel- and lesion-specific scores had higher AUC's as compared to whole-heart values (whole-heart AgSc AUC: 0.58; maximum lesion-specific volume score AUC: 0.72). Statistically defined, optimal cut-point for whole-heart AgSc was 986; corresponding sensitivity and specificity were 32% and 93%. Optimal cut-point for maximum lesion-specific VolSc was 132 with 51% sensitivity and 88% specificity. A similar pattern was also seen for the prediction of ≥70% stenosis by XRA, although the performance of whole-heart AgSc improved (AUC 0.66) as compared to ≥50% stenosis.

FIG. 10 depicts the ROC curve analysis associated with the ROC curve of FIG. 9, where WH is whole-heart; VS is volume-specific; Max LS is maximum lesion-specific; Mean LS is mean of lesion-specific; AUC is area under ROC curve; Sens is sensitivity; Spec is specificity; PPV is the positive predictive value; and NPV is negative predictive value. Cut-points were selected to achieve maximum summation of sensitivity and specificity. Conventional cut-points of 100 and 400 of WH-AgSc were also tested.

Since the "optimal cut-point" of 986 for whole-heart AgSc is not very clinically meaningful, the diagnostic performance of each of the parameters with either sensitivity or specificity fixed at 80% was examined (see Tables 7 and 8). This analysis showed that when sensitivity was fixed at 80%, specificity increased from 22.2% (whole-heart AgSc) to 42.1% (maximum lesion-specific VolSc) for the detection of ≥50% stenosis; for the detection of ≥70% stenosis, specificity increased from 43.1% (whole-heart AgSc) to 62.1% (maximum lesion-specific VolSc). When specificity was fixed at 80%, sensitivity increased from 35.1% (whole-heart AgSc) to 61.4% (vessel-specific VolSc) for the detection of 50% stenosis; for the detection of ≥70% stenosis, sensitivity increased from 48.5% (whole-heart AgSc) to 61.1% (maximum lesion-specific AgSc).

TABLE 7

Comparison of CAC predictive values while specificities are fixed at 80%.

| | 50% stenosis | | | | | 70% stenosis | | | | |
|---|---|---|---|---|---|---|---|---|---|---|
| | Cut-point | Sens | Spec | PPV | NPV | Cut-point | Sens | Spec | PPV | NPV |
| WH-AgSc | 790 | 35.1% | 80% | 80% | 37.3% | 770 | 48.5% | 80% | 61.5% | 70.7% |
| WH-VolSc | 661 | 36.8% | 80% | 80.8% | 37.9% | 661 | 48.5% | 80% | 61.5% | 70.7% |
| VS-AgSc | 194 | 60.2% | 80% | 61% | 79.9% | 264 | 61.1% | 80% | 34.9% | 92.2% |
| VS-VolSc | 158 | 61.4% | 80% | 61.4% | 79.4% | 238 | 58.3% | 80% | 33.9% | 91.7% |
| Max LS-AgSc | 119 | 56.6% | 80% | 59.5% | 77.9% | 155 | 61.1% | 80% | 34.9% | 92.2% |
| Max LS-VolSc | 97 | 55.4% | 80% | 59% | 77.4% | 127 | 61.1% | 80% | 34.9% | 92.2% |

TABLE 7-continued

Comparison of CAC predictive values while specificities are fixed at 80%.

|  | 50% stenosis | | | | | 70% stenosis | | | | |
| --- | --- | --- | --- | --- | --- | --- | --- | --- | --- | --- |
|  | Cut-point | Sens | Spec | PPV | NPV | Cut-point | Sens | Spec | PPV | NPV |
| Mean LS-AgSc | 63 | 48.2% | 80% | 55.6% | 74.7% | 76 | 55.6% | 80% | 32.8% | 91.2% |
| Mean LS-VolSc | 53 | 48.2% | 80% | 55.6% | 74.7% | 67 | 52.8% | 80% | 31.7% | 90.7% |

WH: whole-heart;
VS: volume-specific;
Max LS: maximum lesion-specific;
Mean LS: mean of lesion-specific;
AUC: area under ROC curve;
Sens: sensitivity;
Spec: specificity;
PPV: positive predictive value;
NPV: negative predictive value.

TABLE 8

Comparison of CAC predictive values while sensitivities are fixed at 80%.

|  | 50% stenosis | | | | | 70% stenosis | | | | |
| --- | --- | --- | --- | --- | --- | --- | --- | --- | --- | --- |
|  | Cut-point | Sens | Spec | PPV | NPV | Cut-point | Sens | Spec | PPV | NPV |
| WH-AgSc | 71 | 80% | 22.2% | 68.7% | 35.3% | 232 | 80% | 43.1% | 48.2% | 78.6% |
| WH-VolSc | 63 | 80% | 22.2% | 68.7% | 35.3% | 127 | 80% | 41.2% | 47.4% | 77.8% |
| VS-AgSc | 34 | 80% | 35.8% | 39.6% | 78.1% | 114 | 80% | 63.1% | 27.6% | 94.9% |
| VS-VolSc | 47 | 80% | 42.1% | 42.1% | 80.7% | 110 | 80% | 60.7% | 26.4% | 94.7% |
| Max LS-AgSc | 34 | 80% | 40.3% | 41.4% | 80.0% | 78 | 80% | 59.7% | 25.9% | 94.6% |
| Max LS-VolSc | 31 | 80% | 42.1% | 42.1% | 80.7% | 71 | 80% | 62.1% | 27.1% | 94.8% |
| Mean LS-AgSc | 20 | 80% | 44% | 42.9% | 81.4% | 24 | 80% | 45.1% | 20.4% | 93.0% |
| Mean LS-VolSc | 18 | 80% | 42.1% | 42.1% | 80.7% | 23 | 80% | 46.6% | 20.9% | 93.2% |

WH: whole-heart;
VS: volume-specific;
Max LS: maximum lesion-specific;
Mean LS: mean of lesion-specific;
AUC: area under ROC curve;
Sens: sensitivity;
Spec: specificity;
PPV: positive predictive value;
NPV: negative predictive value.

Classification of Patients

Another measure of improved diagnostic accuracy is the overall correct classification of patients. Assuming that the 80% sensitivity and specificity cut-points are clinically meaningful and patients above and below the respective cut-points are considered positive or negative and those who fall between those values are indeterminate, the proportion of indeterminate patients significantly decreased with the lesion-specific approach from 50% to only 17.9%, compared to the whole-heart AgSc.

This study tested the hypothesis that a more detailed analysis of CAC datasets based on vessel- and lesion-specific measurements has superior diagnostic accuracy for the prediction of obstructive CAD, using invasive coronary angiography as reference standard. Indeed, the main finding of this study was that maximum lesion-specific AgSc resulted in a significantly increased diagnostic accuracy compared to the whole-heart Agatston score, as evidenced by a higher AUC on ROC analysis (0.72 vs 0.58). Therefore, when specificity was fixed at 80%, as often necessary in clinical practice, sensitivity of vessel- and lesion-specific values increased by about 20%, which is a clinically significant improvement.

The whole-heart Agatston and volume scores are a simple summation of all calcified lesions in the three major epicardial arteries and are therefore inherently limited in the geographic localization of specific stenoses. Accordingly, in this study, whole-heart AgSc and VolSc were not different in patients with and without obstructive CAD, when CAD was defined based on 50% stenosis. Furthermore, the diagnostic accuracy of whole-heart AgSc and VolSc based on ROC analysis was poor for the prediction of obstructive CAD, either using 50% or 70% to define obstructive CAD (FIG. 10).

However, the 3-dimensional CAC dataset contains significantly more information beyond the whole-heart Agatston and volume scores and therefore has the potential to improve diagnostic accuracy. Indeed, both for the detection of 50% and 70% stenoses, the AUC for vessel- and lesion-specific values were greater than 0.70, compared to the AUC of 0.58 for whole-heart AgSc.

The diagnostic performance of both vessel-specific and lesion-specific parameters were evaluated. Based on AUC calculations alone, vessel-specific parameters were slightly better than lesion-specific values both for the prediction of 50% and 70% stenosis (FIG. 10). For lesion-specific parameters, maximum values were better than means (FIG. 10). Comparing the sensitivities of each parameter when specificity was fixed at 80%, vessel-specific AgSc, maximum lesion-specific AgSc and maximum vessel-specific VolSc had the highest sensitivity for the prediction of 70% stenosis by XRA. Since vessel-specific measurements are more readily available on current, clinical, commercial workstations, such measurements may be more practical in clinical practice today. The prediction of obstructive CAD with vessel- and lesion-specific parameters was improved compared to the whole-heart approach, whether 50% of 70% was used for the definition of obstructive CAD, although the degree of improvement was larger for the detection of 50% stenosis.

From a clinical perspective, an AUC of 0.70 or greater—which was seen with all vessel- and lesion-specific parameter—is comparable to other clinically useful diagnostic tests, such as radionuclide myocardial perfusion imaging (87% sensitivity and 73% specificity) or stress echocardiography (70% sensitivity and 89% specificity). Therefore, it is proposed that a vessel- and lesion-specific approach is more acceptable for clinical decision-making as compared to traditional whole-heart AgSc, given the finding of a 61% sensitivity with an 80% specificity.

It is interesting to speculate how vessel- and lesion-specific scores may be incorporated in clinical practice. CAC imaging is currently recommended for asymptomatic subjects without known—but with intermediate likelihood of—CAD for the purposes of refined risk stratification. The apparent paradox is, however, that revascularization is typically reserved for patients with symptoms due to myocardial ischemia and therefore, it has been a clinical challenge to recommend further diagnostic testing on the basis of CAC scanning in asymptomatic subjects. It has been suggested that since many patients may be asymptomatic due to physical inactivity, provocative testing may be performed to uncover potential ischemia in patients with elevated CAC scores (ie. Agatston score 400 or greater). However, as we pointed out earlier, the specificity and positive predictive value of the whole-heart AgSc, whether using a cut-point of 400 or even 1000, are quite low. Therefore, it is proposed that the improved diagnostic accuracy of vessel- and lesion-specific scores may be helpful in refining clinical decision making. As shown, using cut-points for 80% sensitivity (to rule out obstructive CAD) and for 80% specificity (to rule in obstructive CAD), a vessel- and lesion-specific approach significantly reduces the number of patients with an "indeterminate" CAC for the prediction of ≥50% obstructive CAD (FIG. 5). As a potential clinical approach, patients below the cut-point corresponding to 80% sensitivity (eg. vessel-specific VolSc<47) clearly do not need further workup for ischemia or obstructive CAD, while those above the cut-point corresponding to 80% specificity (e.g. vessel-specific VolSc>158) could be referred for myocardial perfusion imaging or for coronary angiography. Those in the intermediate zone could be referred for myocardial perfusion imaging. In this regard, it is important to point out that significantly less patients fall into the intermediate zone using the vessel- and lesion-specific approach, compared to the whole-heart Agatston score.

Although to our knowledge, no previous investigation has evaluated the diagnostic accuracy of a vessel- and lesion-specific approach, the Calcium Coverage Score (CCS) has been previously introduced to improve the predictive value of CAD events beyond the whole-heart Agatston score. In a study, Brown et al. showed that the percentage of coronary arteries affected by calcific plaque was significantly associated with coronary heart disease events. However, there was no difference in the prediction of hard cardiac events (myocardial infarction or death) when CCS was compared to the whole-heart Agatston and mass scores.

The study showed that a lesion-specific CAC approach was superior to the whole-heart AgSc in the prediction of obstructive CAD, using invasive coronary angiography as a reference standard. Such an approach may also be superior for the detection of obstructive CAD using intravascular ultrasound as reference standard, and even for the prediction of a hemodynamically significant stenosis, as measured by fractional flow reserve (FFR).

While various embodiments of the present system and method have been described above, it should be understood that the embodiments have been presented by the way of example only, and not limitation. It will be understood by those skilled in the art that various changes in form and details may be made therein without departing from the spirit and scope of the invention as defined. Thus, the breadth and scope of the present invention should not be limited by any of the above described exemplary embodiments.

What is claimed is:

1. A method for predicting the risk of a coronary event for a human comprising:
   generating a non-contrast-enhanced volumetric image of the cardiac region of the human utilizing a computed tomography coronary artery calcium scan generated by a computed tomography scanner;
   storing said volumetric image in a storage device as stored volumetric data, where said storage device is operably connected to a processor adapted to load and process said stored volumetric data;
   transforming said stored volumetric data to a binary calcium volume data by applying an intensity threshold to said stored volumetric data using said processor;
   processing said stored volumetric data to identify a calcific lesion within said stored volumetric data, wherein the calcific lesion is identified by processing the volumetric data in a three-dimensional (3D) form instead of a two-dimensional (2D) form;
   measuring geometric and morphologic characteristics of said calcific lesion based at least in part on said stored volumetric data;
   measuring a distance between said calcific lesion and the origin of the coronary artery said calcific lesion is occluding based at least in part on said stored volumetric data; and
   estimating a risk profile based on said geometric and morphologic characteristics and said distance, wherein a risk of the risk profile is increased as the distance between the calcific lesion and the origin of the coronary artery said calcific lesion is occluding is decreased.

2. The method of claim 1, further comprising:
   assessing whole heart risk of a heart in the cardiac region based at least in part upon a 3D Agatston score of the binary calcium volume data; and
   assessing likelihood of a particular coronary event in a specific region of the heart.

3. The method of claim 1, further comprising presenting to a user an overlaid image comprising a color-coded calcium volume image over a gray-scale image of said stored volumetric data.

4. The method of claim 1, wherein said intensity threshold is selected to maximize a contrast of calcific regions.

5. The method of claim 1, further comprising identifying an origin of an artery in the non-contrast-enhanced volumetric image of the cardiac region and estimating a probability of a coronary event based at least in part on the distance between said calcific lesion and said origin.

6. The method of claim 5, further comprising adjusting said probability based at least in part on a measured width of said calcific lesion.

7. The method of claim 1, further comprising volumetrically identifying a 3D volume of said calcific lesion at least in part by performing a volumetric fill of the region sounding a point within said stored volumetric data.

8. The method of claim 7, further comprising determining first and third eigenvectors of said 3D volume wherein said first eigenvector is substantially aligned with said artery and said third eigenvector is substantially perpendicular to said artery.

9. The method of claim 8, further comprising:
   i. estimating a maximum length of said 3D volume projected along the first eigenvector; and
   ii. estimating a maximum width of said 3D volume projected along said third eigenvector.

10. The method of claim 7, further comprising de-noising said 3D volume by eliminating any continuous regions within the stored binary calcium data with a total volume of less than about 1 mm^3.

11. The method of claim 7, further comprising determining a lesion density by averaging said calcific density in said 3D volume.

12. The method of claim 11, further comprising calculating a 3D Agatston score corresponding to said calcific lesion using at least said lesion density.

13. The method of claim 11, further comprising estimating a cardiac risk factor attributable to an arterial branch of said cardiac region by summing said 3D Agatston scores for each of said calcific lesions associated with said arterial branch.

14. The method of claim 13, further comprising
   i. calculating a whole heart 3D Agatston score by summing said 3D Agatston scores for each of said calcific lesions;
   ii. determining a maximum 3D Agatston score;
   iii. estimating a lesion distance between each of said calcific lesions and an origin of the respective arterial branch where said calcific lesion is located; and,
   iv. estimating likelihood of cardiac event based at least in part on said whole heart 3D Agatston score, said maximum 3D Agatston score, or said lesion distance.

15. The method of claim 7, wherein performing the volumetric fill comprises executing a 6-connectiveness 3D operation.

16. The method of claim 1, wherein said processing said stored volumetric data to identify said calcific lesion comprises identifying a plurality of voxels represented in said stored volumetric data that correspond to said calcific lesion.

17. The method of claim 16, wherein said identifying said plurality of voxels comprises determining one or more voxels adjacent to a selected voxel having a value within a predetermined range of the selected voxel.

18. The method of claim 16, wherein said measuring said geometric and morphologic characteristics of said calcific lesion is based at least in part on said plurality of voxels and a determined resolution of said volumetric image.

19. The method of claim 16, wherein said measuring said distance between said calcific lesion and said origin of said coronary artery said lesion is occluding is based at least in part on said plurality of voxels and a determined resolution of said volumetric image.

20. A method for predicting the risk of a coronary event for a human comprising:
   performing a computed tomography coronary artery calcium scan on the human;
   generating a non-contrast-enhanced volumetric image of the cardiac region of the human;
   storing said volumetric image in a storage device as stored volumetric data, where said storage device is operably connected to a processor adapted to load and process said stored volumetric data;
   processing said stored volumetric data to identify at least one calcific lesion within said stored volumetric data for analysis, wherein the calcific lesion is identified by processing the volumetric data in a three-dimensional (3D) form instead of a two-dimensional (2D) form;
   selecting an intensity threshold of said stored volumetric data lesion via said processor;
   transforming said stored volumetric data to a stored binary calcium volume data by applying said intensity threshold to said stored volumetric data using said processor;
   identifying said calcific lesion within said binary calcium volume;
   measuring geometric and morphologic characteristics of said calcific lesion based at least in part on said stored volumetric data;
   measuring a distance between said calcific lesion and the origin of the coronary artery said lesion is occluding based at least in part on said stored volumetric data; and
   estimating a risk profile based on said geometric and morphologic characteristics and said distance, wherein a risk of the risk profile is increased as the distance between the calcific lesion and the origin of the coronary artery said calcific lesion is occluding is decreased.

21. The method of claim 20, further comprising:
   assessing whole heart risk of a heart in the cardiac region based at least in part upon a 3D Agatston score of the stored binary calcium volume data; and
   assessing likelihood of a particular coronary event in a specific region of the heart.

22. The method of claim 20, further comprising volumetrically identifying a 3D volume of said calcific lesion by performing a volumetric fill of the region sounding a point within said stored volumetric data.

23. The method of claim 22, wherein performing the volumetric fill comprises executing a 6-connectiveness 3D operation.

24. The method of claim 20, wherein said processing said stored volumetric data to identify said calcific lesion comprises identifying a plurality of voxels represented in said stored volumetric data that correspond to said calcific lesion.

25. The method of claim 24, wherein said identifying said plurality of voxels comprises determining one or more voxels adjacent to a selected voxel having a value within a predetermined range of the selected voxel.

26. The method of claim 24, wherein said measuring said geometric and morphologic characteristics of said calcific lesion is based at least in part on said plurality of voxels and a determined resolution of said volumetric image.

27. The method of claim 24, wherein said measuring said distance between said calcific lesion and said origin of said coronary artery said lesion is occluding is based at least in part on said plurality of voxels and a determined resolution of said volumetric image.

* * * * *

UNITED STATES PATENT AND TRADEMARK OFFICE
CERTIFICATE OF CORRECTION

PATENT NO. : 8,970,578 B2  Page 1 of 1
APPLICATION NO. : 12/643962
DATED : March 3, 2015
INVENTOR(S) : Szilard Voros and Zhen Qian It is certified that error appears in the above-identified patent and that said Letters Patent is hereby corrected as shown below:

In the claims,

Column 17, Line 7 "20%±30% higher than the whole-heart scores." should read -- 20% ~ 30% higher than the whole-heart scores. --.

Column 17, Line 24 "that 36 is the cutoff point of the Gaussian model, then most of" should read -- $3\sigma$ is the cutoff point of the Gaussian model, then most of --.

Signed and Sealed this
Twenty-ninth Day of December, 2015

Michelle K. Lee
*Director of the United States Patent and Trademark Office*